United States Patent
Robinson

(10) Patent No.: US 7,041,500 B2
(45) Date of Patent: May 9, 2006

(54) INSECT CELL LINE

(75) Inventor: Robin A. Robinson, Dickerson, MD (US)

(73) Assignee: Novavax, Inc., Malvern, PA (US)

( * ) Notice: Subject to any disclaimer, the term of this patent is extended or adjusted under 35 U.S.C. 154(b) by 84 days.

(21) Appl. No.: 10/367,095

(22) Filed: Feb. 14, 2003

(65) Prior Publication Data

US 2003/0228696 A1 Dec. 11, 2003

Related U.S. Application Data

(60) Provisional application No. 60/356,119, filed on Feb. 14, 2002, provisional application No. 60/356,161, filed on Feb. 14, 2002, provisional application No. 60/356,118, filed on Feb. 14, 2002, provisional application No. 60/356,157, filed on Feb. 14, 2002, provisional application No. 60/356,156, filed on Feb. 14, 2002, provisional application No. 60/356,123, filed on Feb. 14, 2002, provisional application No. 60/356,113, filed on Feb. 14, 2002, provisional application No. 60/356,154, filed on Feb. 14, 2002, provisional application No. 60/356,135, filed on Feb. 14, 2002, provisional application No. 60/356,126, filed on Feb. 14, 2002, provisional application No. 60/356,162, filed on Feb. 14, 2002, provisional application No. 60/356,150, filed on Feb. 14, 2002, provisional application No. 60/356,151, filed on Feb. 14, 2002, provisional application No. 60/356,152, filed on Feb. 14, 2002.

(51) Int. Cl.
*C12N 5/16* (2006.01)

(52) U.S. Cl. .................................. 435/348; 435/235.1

(58) Field of Classification Search ................ 435/348, 435/235.1
See application file for complete search history.

(56) References Cited

OTHER PUBLICATIONS

Bosch, F.X. et al. "Prevalence of human paillomavirus in cervical cancer: a worldwide perspective." *Journal of the National Cancer Institute* 87(11):796-802 (1995).

Breitburd, F. et al. "Immunization with viruslike particles from cottontail rabbit papillomavirus (CRPV) can protect against experimental CPRV infection." *Journal of Virology* 69(6):3959-3963 (1995).

Christensen, N.D. et al. "Assembled baculovirus-expressed human papillomavirus type 11 L1 capsid protein virus-like particles are recognized by neutralizing monoclonal antibodies and induce high titres of neutralizing antibodies." *Journal of General Virology* 75:2271-2276 (1994).

Christensen, N.D. et al. "Immunization with viruslike particles induces long-term protection of rabbits against challenge with cottontail rabbit papillomavirus." *Journal of Virology* 70:960-965 (1996).

Cook, J.C. et al. "Purification of virus-like particles of recombinant human papillomavirus type 11 major capsid protein L1 from *Saccharomyces cerevisiae*." *Protein Expression and Purification* 17:477-484 (1999).

Greenstone, H.L. et al. "Chimeric papillomavirus virus-like particles elicit antitumor immunity against the E7 oncoprotein in an HPV16 tumor model." *Proc. Natl. Acad. Sci. USA* 95:1800-1805 (1998).

Harro, C.D. et al. "Safety and immunogenicity trial in adult volunteers of a human papillomavirus 16 L1 virus-like particle vaccine." *Journal of the National Cancer Institute* 93(40):248-292 (2001).

Joyce, J.G. et al. "The L1 major capsid protein of human papillomavirus type 11 recombinant virus-like particles interacts with heparin and cell-surface glycosaminoglycans on human keratinocytes." *Journal of Biological Chemistry* 274(9):5810-5822 (1999).

Kirnbauer, R. et al. "Papillomavirus L1 major capsid protein self-assembles into virus-like particles that are highly immunogenic." *Proc. Natl. Acad. Sci. USA* 89:12180-12184 (1992).

Kirnbauer, R. et al. "Efficient self-assembly of human papillomavirus type 16 L1 and L1-L2 into virus-like particles." *Journal of Virology* 67(12):6929-6936 (1993).

Levin, D.B. et al. "Codon usage in nucleopolyhedroviruses." *Journal of General Virology* 81:2313-2325 (2000).

(Continued)

*Primary Examiner*—James Ketter
(74) *Attorney, Agent, or Firm*—Edwards Angell Palmer & Dodge, LLP; Ralph A. Loren

(57) ABSTRACT

An insect cell line capable of growth in serum-free media and secretion of high levels of recombinant proteins, including virus-like particles, upon infection with recombinant baculoviruses, is provided. Methods involving clonal selection processes, serum-weaning and recombinant protein secretion selection are used to create the insect lines of the invention. This cell line supports replication of baculoviruses, serves as host substrate for baculovirus plaque assays, provides a source of insect proteins, acts as a depot for cell transfection to produce recombinant baculoviruses, and express viral recombinant proteins. Extracellular and intracellular viral recombinant proteins and virus-like particles expressed from this cell line are useful as pharmaceutical compositions, vaccines, or diagnostic reagents.

9 Claims, 15 Drawing Sheets

OTHER PUBLICATIONS

Lowy, D.R. et al. "Chapter 66: Papillomaviruses." in Knipe, D.M. et al. Eds. *Fields Virology*, 4th Ed. vol. 2, Lippincott Williams & Wilkins, Philadelphia, PA pp. 2231-2264 (2001).

Luckow, V.A. et al. "Efficient generation of infectious recombinant baculoviruses by site-specific transposon-mediated insertion of foreign genes into a baculovirus genome propagated in *Escherichia coli.*" *Journal of Virology* 67(8):4566-4579 (1993).

O'Neil, P.F. et al. "Virus harvesting and affinity-based liquid chromatography." *Biotechnology* 11:173-178 (1993).

Parkin, D.M. et al. "Estimates of the worldwide incidence of 25 major cancers in 1990." *Int. J. Cancer* 80:827-841 (1999).

Pisani, P. et al. "Estimates of the worldwide mortality from 25 cancers in 1990." *Int. J. Cancer* 83:18-29 (1999).

Robinson, R.A. et al. "Structural characterization of recombinant hepatitis E virus ORF2 proteins in baculovirus-infected insect cells." *Protein Expression and Purification* 12:75-84 (1998).

Rose, R.C. et al. "Expression of human papillomavirus type 11 L1 protein in insect cells: *in vivo* and *in vitro* assembly of viruslike particles." *Journal of Virology* 67(4):1936-44 (1993).

Schiller, J.T. et al. "Papillomavirus-like particles and HPV vaccine development." *Seminars in Cancer Biology* 7:373-382 (1996).

Suzich, J.A. et al. "Systemic immunization with papillomavirus L1 protein completely prevents the development of viral mucosal papillomas." *Proc. Natl. Acad. Sci. USA* 92:11553-11557 (1995).

Walboomers, J.M.M. et al. "Human papillomavirus is a necessary cause of invasive cervical cancer worldwide." *Journal of Pathology* 189:12-19 (1999).

Zhou, J. et al. "Synthesis and assembly of infectious bovine papillomavirus particles *in vitro.*" *Journal of General Virology* 74(4):763-768 (1993).

SEQUENCE LISTING

<160> NUMBER OF SEQ ID NOS: 13
<210> SEQ ID NO 1
<211> LENGTH: 1515
<212> TYPE: DNA
<213> ORGANISM: Artificial Sequence
<220> FEATURE:
<223> OTHER INFORMATION: HPV-16 L1 codon optimized sequence

<400> SEQUENCE: 1

```
atgtccctct ggctgccctc cgaggccacc gtctacctcc ccccgtccc cgtctccaag      60 gtcgtctcca ccgatgaata cgtcgctcgc accaacatct actaccatgc tggtacctcc    120
cgtctcctgg ctgtcggtca tccctacttc cccatcaaga agcccaacaa caacaagatc    180
ctcgtcccca aggtctccgg tctccaagtc cgtgtcttcc gtatccatct ccccgacccc    240
aacaagttcg gtttccccga cacctccttc tacaaccccg atacccagcg cctgtactgg    300
gcctgcgtcg gtgtcgaggt cggtcgtggt cagcccctcg gtgtcggcat ctccggccac    360 ccctcctca acaagctcga cgacaccgag aacgcctccg cctacgccgc caacgccggt    420
gtcgacaacc gtgagtgcat ctccatggac tacaagcaga cccagctctg cctcatcggt    480
tgcaagcccc ccatcggtga gcactgggGt aagggttccc cctgcaccaa cgtcgccgtc    540 aacccggtg actgcccccc cctcgagctc atcaacaccg tcatccagga cggtgacatg    600
gtcgacaccg gtttcggtgc catggacttc accaccctcc aggccaacaa gtccgaggtc    660 ccctcgaca tctgcacctc catctgcaag taccccgact acatcaagat ggtctccgag    720
ccctacggtg actccctctt cttctacctc cgccgcgagc agatgttcgt ccgccacctc    780
ttcaaccgcg ccggtgctgt cggtgagaac gtccccgacg acctctacat caagggttcc    840
ggttccaccg ccaacctcgc ttcctccaac tacttcccca ccccctccgg ttccatggtc    900
acctccgacg cccagatctt caacaagccc tactggctcc agcgcgctca gggtcacaac    960
aacggtatct gctgggGtaa ccagctcttc gtcaccgtcg tcgacaccac ccgctccacc   1020
aacatgtccc tctgcgccgc catctccacc tccgagacca cctacaagaa caccaacttc   1080
aaggagtacc tccgccacgg tgaggagtac gacctccagt tcatcttcca gctctgcaag   1140
atcaccctca ccgccgacgt catgacctac atccactcca tgaactccac catcctcgag   1200
gactggaact tcggtctcca gccccccccc ggtggtaccc tcgaggacac ctaccgcttc   1260
gtcacctccc aggccatcgc ctgccagaag cacaccccc ccgccccaa ggaggacccc   1320 ctcaagaagt acaccttctg ggaggtcaac ctcaaggaga gttctccgc cgacctcgac   1380 cagttccccc tcggtcgcaa gttcctcctc caggccggtc tcaaggccaa gcccaagttc   1440
accctcggta gcgcaaggc cacccccacc acctcctcca cctccaccac cgccaagcgc   1500
aagaagcgca agctc                                                    1515
```

<210> SEQ ID NO 2
<211> LENGTH: 1413
<212> TYPE: DNA
<213> ORGANISM: Artificial Sequence
<220> FEATURE:
<223> OTHER INFORMATION: HPV-16 L2 codon optimized sequence

<400> SEQUENCE: 2

| | |
|---|---|
| atgcgtcaca agcgttccgc caagcgtacc aagcgtgcct ccgccaccca gctctacaag | 60 |
| acctgcaagc aggccggtac ctgccccccc gacatcatcc caaggtcga gggtaagacc | 120 |
| atcgccgacc agatcctcca gtacggttcc atgggtgtct tcttcggtgg tctcggtatc | 180 |
| ggtaccggtt ccggtaccgg tggtcgtacc ggttacatcc cctcggtac ccgtccccc | 240 |
| accgccaccg acaccctcgc cccgtccgt cccccctca ccgtcgaccc cgtcggtccc | 300 |
| tccgacccct ccatcgtctc cctcgtcgag gagacctcct tcatcgacgc cggtgccccc | 360 |
| acctccgtcc cctccatccc cccgacgtc tccggcttct ccatcaccac ctccaccgac | 420 |
| accaccccg ccatcctcga catcaacaac accgtcacca ccgtcaccac ccacaacaac | 480 |
| cccaccttca ccgaccccctc cgtcctccag ccccccaccc ccgccgagac cggtggtcac | 540 |
| ttcaccctct cctcctccac catctccacc cacaactacg aggagatccc catggacacc | 600 |
| tttatcgtct ccaccaaccc caacaccgtc acctcctcca ccccccatccc cggttcccgt | 660 |
| cccgtcgccc gtctgggcct ctactcccgt accacccagc aggtcaaggt cgtcgacccc | 720 |
| gccttcgtca ccaccccac caagctcatc acctacgaca ccccgccta cgagggtatc | 780 |
| gacgtcgaca cacccctcta cttctcctcc aacgacaact ccatcaacat cgccccgac | 840 |
| cccgacttcc tcgacatcgt cgccctccac cgtcccgccc tcacctcccg tcgcaccggc | 900 |
| atccgctact cccgtatcgg taacaagcag accctccgta cccgttccgg taagtccatc | 960 |
| ggtgccaagg tccactacta ctacgacttc tccaccatcg accccgccga ggagatcgag | 1020 |
| ctccagacca tcaccccctc cacctacacc accacctccc acgccgcctc ccccacctcc | 1080 |
| atcaacaacg tctctacga catctacgcc gacgacttca tcaccgacac ctccaccacc | 1140 |
| cccgtccct ccgtcccctc cacctccctc tccggttaca tccccgccaa caccaccatc | 1200 |
| cccttcggtg cgcctacaa catcccctc gtctccggtc ccgacatccc catcaacatc | 1260 |
| accgaccagg cccctccct catccccatc gtccccggct cccccagta caccatcatc | 1320 |
| gccgacgccg tgacttcta cctccacccc tcctactaca tgctccgtaa gcgtcgtaag | 1380 |
| cgtctccccct acttcttctc cgacgtctcc tga | 1413 |

<210> SEQ ID NO 3
<211> LENGTH: 1466
<212> TYPE: DNA
<213> ORGANISM: Artificial Sequence
<220> FEATURE:
<223> OTHER INFORMATION: HPV-16 L2/E7 fusion gene codon optimized
    sequence

<400> SEQUENCE: 3

| | |
|---|---|
| atatgcgaca caaacgttct gcaaaacgca caaaacgtgc atcggccacc caactttata | 60 |
| aaacatgcaa acaggcaggt acatgtccac ctgacattat acctaaggtt gaaggcaaaa | 120 |
| ctattgctga tcaaatatta caatatggaa gtatgggtgt attttttggt gggttaggaa | 180 |
| ttggaacagg gtctggtaca ggcgacgca ctgggtatat ccattgggaa caaggcctc | 240 |
| ccacagctac agatacactt gctcctgtaa gaccccctt aacggtagat cctgtgggcc | 300 |

-continued

| | |
|---|---|
| cttctgatcc gtctatagtt tcgttagtgg aagaaactag ttttattgat gctggtgcac | 360 |
| caacacctgt accttccatt cccccagatg tatcaggatt tagtattaca acttcaactg | 420 |
| ataccacacc tgctatatta gatattaata atactgttac tactgttact acacataata | 480 |
| atcccacttt tactgaccca tctgtattgc agcctccaac acctgcagaa actggagggc | 540 |
| attttacact tcatcatcc actattagta cacataatta tgaagaaatt cctatggata | 600 |
| catttattgt tagcacaaat cctaacacag taactagtag cacacccata ccggggtctc | 660 |
| gcccagtggc acgcctagga ttatatagtc gcaacacaca acaagttaaa gttgtagacc | 720 |
| ctgcttttgt aaccactccc actaaactta ttacatatga taatcctgca tatgaaggta | 780 |
| tagatgtgga taatacatta tattttccta gtaatgataa tagtattaat atagctccag | 840 |
| atcctgactt tttggatata gttgctttac ataggccagc attaacctct aggcgtactg | 900 |
| gcattagata cagtagaatt ggtaataaac aaacactacg tactcgtagt ggaaaatcta | 960 |
| taggtgctaa ggtacattat tattatgatt taagtactat taatcctgca gaagaaatag | 1020 |
| aattgcaaac tataacacct tctacatata ctacccttc acatgcagcc tcacccactt | 1080 |
| ctattaataa tggattatat gatatttatg cagatgactt tattacagat acttttacaa | 1140 |
| ccccagtacc atctataccc tctacatcct tatcaggtta tattcctgca aatacaacaa | 1200 |
| ttccttttgg tggtgcatac aatattcctt tagtatcagg tcctgatata cctattaata | 1260 |
| caactgacca aactccttca ttaattccta tagttccagg tctccacaa tatacaatta | 1320 |
| ttgctgatgg aggtgacttt tatttacatc ctagttatta catgttacga aaacgacgta | 1380 |
| aacgtttacc atattttttt tcagatgtat cgatgcatgg agatacacct acattgcatg | 1440 |
| aatatatgtt agatttgcaa ccagag | 1466 |

<210> SEQ ID NO 4
<211> LENGTH: 2805
<212> TYPE: DNA
<213> ORGANISM: Artificial Sequence
<220> FEATURE:
<223> OTHER INFORMATION: HPV-16 L2/E7/E2 fusion gene codon optimized
    sequence

<400> SEQUENCE: 4

| | |
|---|---|
| atgcgacaca acgttctgc aaaacgcaca aacgtgcat cggctaccca actttataaa | 60 |
| acatgcaaac aggcaggtac atgtccacct gacattatac ctaaggttga aggcaaaact | 120 |
| attgctgatc aaatattaca atatggaagt atgggtgtat tttttggtgg gttaggaatt | 180 |
| ggaacagggt cgggtacagg cggacgcact gggtatattc cattgggaac aaggcctccc | 240 |
| acagctacag atacttgc tcctgtaaga ccccctttaa cagtagatcc tgtgggccct | 300 |
| tctgatccctt ctatagtttc tttagtggaa gaaactagtt ttattgatgc tggtgcacca | 360 |
| acatctgtac cttccattcc ccagatgta tcaggattta gtattactac ttcaactgat | 420 |
| accacacctg ctatattaga tattaataat actgttacta ctgttactac acataataat | 480 |
| cccactttca ctgacccatc tgtattgcag cctccaacac tgcagaaac tggagggcat | 540 |
| tttacacttt catcatccac tattagtaca cataattatg aagaaattcc tatggataca | 600 |
| tttattgtta gcacaaaccc taacacagta actagtagca cccatacc agggtctcgc | 660 |
| ccagtggcac gcctaggatt atatagtcgc aacacaaac aagttaaagt tgtagaccct | 720 |
| gcttttgtaa ccactccac taaacttatt acatatgata tcctgcata tgaaggtata | 780 |
| gatgtgata atacattata ttttctagt aatgataata gtattaatat agctccagat | 840 |

-continued

```
cctgacttttt tggatatagt tgctttacat aggccagcat taacctctag gcgtactggc    900
ataaggtaca gtagaattgg taataaacaa acactacgta ctcgtagtgg aaaatctata    960
ggtgctaagg tacattatta ttatgatttt agtaccattg atcctgcaga agaaatagaa   1020
ttacaaacta taacaccttc tacatatact accacttcac atgcagcctc acctacttct   1080
attaataatg gattatatga tatttatgca gatgacttta ttacagatac ttctacaacc   1140
ccggtaccat ctgtaccctc tacatcttta tcaggttata ttcctgcaaa tacaacaatt   1200
ccttttggtg gtgcatacaa tattccttta gtatcaggtc ctgatatacc cattaatata   1260
actgaccaag ctccttcatt aattcctata gttccagggt ctccacaata taattatt    1320 gctgatgcag gtgactttta tttacatcct agttattaca tgttacgaaa acgacgtaaa   1380
cgtttaccat atttttttc agatgtatcg atgcatggag atacacctac attgcatgaa   1440
tatatgttag atttgcaacc agagacaact gatctctacg ctatgagca attaaatgac   1500 agctcagagg aggaggatga aatagatggt ccagctggac aagcagaacc ggacagagcc   1560
cattacaata ttgtaacctt ttgttgcaag tgtgactcta cgcttcggtt gtgcgtacaa   1620
agcacacacg tagacattcg tactttggaa gacctgttaa tgggcacact aggaattgtg   1680
tgccccatct gttctcagaa accatcgatg gagactcttt gccaacgttt aaatgtgtgt   1740
caggacaaaa tactaacaca ttatgaaaat gatagtacag acctacgtga ccatatagac   1800
tattggaaac acatgcgcct agaatgtgct atttattaca aggccagaga aatgggattt   1860
aaacatatta ccaccaggt ggtgccaaca ctggctgtat caagaataaa agcattacaa   1920
gcaattgaac tgcaactaac gttagaaaca atatataact cacaatatag taatgaaaag   1980
tggacattac aagacgttag ccttgaagtg tatttaactg caccaacagg atgtataaaa   2040
aaacatggat atacagtgga agtgcagttt gatggagaca tatgcaatac aatgcattat   2100
acaaactgga cacatatata tatttgtgaa gaagcatcag taactgtggt agagggtcaa   2160
gttgactatt atggtttata ttatgttcat gaaggaatac gaacatattt tgtgcagttt   2220
aaagatgatg cagaaaaata tagtaaaaat aaagtatggg aagttcatgc gggtggtcag   2280
gtaatattat gtcctacatc tgtgtttagc agcaacgaag tatcctctcc tgaaattatt   2340
aggcagcact tggccaacca ctccgccgcg acccatacca aagccgtcgc cttgggcacc   2400
gaagaaacac agacgactat ccagcgacca agatcagagc cagacaccgg aaaccctgc    2460 cacaccacta gttgttgca cagagactca gtggacagtg ctccaatcct cactgcattt   2520
aacagctcac acaaaggacg gattaactgt aatagtaaca ctacacccat agtacattta   2580
aaagtggatg ctaatacttt aaaatgttta agatatagat ttaaaaagca ttgtacattg   2640
tatactgcag tgtcgtctac atggcattgg acaggacata atgtaaaaca taaaagtgca   2700
attgttacac ttcatatga tagtgaatgg caacgtgacc aattttttgtc tcaagttaaa   2760 ataccaaaaa ctattacagt gtctactgga tttatgtcta tatga                  2805
```

<210> SEQ ID NO 5
<211> LENGTH: 1611
<212> TYPE: DNA
<213> ORGANISM: Artificial Sequence
<220> FEATURE:
<223> OTHER INFORMATION: HPV-16 L2/E6 fusion gene codon optimized
     sequence

<400> SEQUENCE: 5

```
atgcgtcaca agcgttccgc caagcgtacc aagcgtgcct ccgccaccca gctctacaag    60
```

```
acctgcaagc aggccggtac ctgccccccc gacatcatcc caaggtcga gggtaagacc    120
atcgccgacc agatcctcca gtacggttcc atgggtgtct tcttcggtgg tctcggtatc    180
ggtaccggtt ccggtaccgg tggtcgtacc ggttacatcc cctcggtac ccgtcccccc    240
accgccaccg acaccctcgc ccccgtccgt ccccccctca ccgtcgaccc cgtcggtccc    300
tccgacccct ccatcgtctc cctcgtcgag gagacctcct tcatcgacgc cggtgccccc    360
acctccgtcc cctccatccc ccccgacgtc tccggcttct ccatcaccac ctccaccgac    420
accaccccg ccatcctcga catcaacaac accgtcacca ccgtcaccac ccacaacaac    480
cccaccttca ccgacccctc cgtcctccag ccccccaccc ccgccgagac cggtggtcac    540
ttcaccctct cctcctccac catctccacc cacaactacg aggagatccc catggacacc    600
tttatcgtct ccaccaaccc caacaccgtc acctcctcca ccccatccc cggttcccgt    660
cccgtcgccc gtctgggcct ctactcccgt accacccagc aggtcaaggt cgtcgacccc    720
gccttcgtca ccaccccac caagctcatc acctacgaca ccccgccta cgagggtatc    780
gacgtcgaca cacctctca cttctcctcc aacgacaact ccatcaacat cgcccccgac    840
cccgacttcc tcgacatcgt cgccctccac cgtcccgccc tcacctcccg tgcaccggc    900
atccgctact cccgtatcgg taacaagcag accctccgta cccgttccgg taagtccatc    960
ggtgccaagg tccactacta ctacgacttc tccaccatcg accccgccga ggagatcgag   1020
ctccagacca tcaccccctc cacctacacc accacctccc acgccgcctc ccccacctcc   1080
atcaacaacg tctctacga catctacgcc gacgacttca tcaccgacac ctccaccacc   1140
cccgtcccct ccgtcccctc cacctccctc tccggttaca tccccgccaa caccaccatc   1200
cccttcggtg cgcctacaa catccccctc gtctccggtc ccgacatccc catcaacatc   1260
accgaccagg cccctcct catccccatc gtccccggct cccccagta ccatcatc     1320
gccgacgccg gtgacttcta cctccacccc tcctactaca tgctccgtaa gcgtcgtaag   1380
cgtctcccct acttcttctc cgacgtctcc atgcaccaga agcgtaccgc catgttccag   1440
gaccccccagg agcgtccccg taagctcccc cagctctgca ccgagctcca gaccaccatc   1500
cacgacatca tcctcgagtg cgtctactgc aagcagcagc tcctgcgtcg tgaggtctac   1560
gacttcgctt ccgcgacct ctgcatcgtc taccgtgacg gcaacccctg a             1611
```

<210> SEQ ID NO 6
<211> LENGTH: 505
<212> TYPE: PRT
<213> ORGANISM: Artificial Sequence
<220> FEATURE:
<223> OTHER INFORMATION: HPV-16 L1 protein

<400> SEQUENCE: 6

```
Met Ser Leu Trp Leu Pro Ser Glu Ala Thr Val Tyr Leu Pro Pro Val
 1               5                  10                  15

Pro Val Ser Lys Val Val Ser Thr Asp Glu Tyr Val Ala Arg Thr Asn
             20                  25                  30

Ile Tyr Tyr His Ala Gly Thr Ser Arg Leu Leu Ala Val Gly His Pro
         35                  40                  45

Tyr Phe Pro Ile Lys Lys Pro Asn Asn Asn Lys Ile Leu Val Pro Lys
     50                  55                  60

Val Ser Gly Leu Gln Tyr Arg Val Phe Arg Ile His Leu Pro Asp Pro
65                  70                  75                  80

Asn Lys Phe Gly Phe Pro Asp Thr Ser Phe Tyr Asn Pro Asp Thr Gln
                 85                  90                  95
```

-continued

```
Arg Leu Val Trp Ala Cys Val Gly Val Glu Val Gly Arg Gly Gln Pro
            100                 105                 110
Leu Gly Val Gly Ile Ser Gly His Pro Leu Leu Asn Lys Leu Asp Asp
        115                 120                 125
Thr Glu Asn Ala Ser Ala Tyr Ala Ala Asn Ala Gly Val Asp Asn Arg
    130                 135                 140
Glu Cys Ile Ser Met Asp Tyr Lys Gln Thr Gln Leu Cys Leu Ile Gly
145                 150                 155                 160
Cys Lys Pro Pro Ile Gly Glu His Trp Gly Lys Gly Ser Pro Cys Thr
                165                 170                 175
Asn Val Ala Val Asn Pro Gly Asp Cys Pro Pro Leu Glu Leu Ile Asn
            180                 185                 190
Thr Val Ile Gln Asp Gly Asp Met Val Asp Thr Gly Phe Gly Ala Met
        195                 200                 205
Asp Phe Thr Thr Leu Gln Ala Asn Lys Ser Glu Val Pro Leu Asp Ile
    210                 215                 220
Cys Thr Ser Ile Cys Lys Tyr Pro Asp Tyr Ile Lys Met Val Ser Glu
225                 230                 235                 240
Pro Tyr Gly Asp Ser Leu Phe Phe Tyr Leu Arg Arg Glu Gln Met Phe
                245                 250                 255
Val Arg His Leu Phe Asn Arg Ala Gly Ala Val Gly Glu Asn Val Pro
            260                 265                 270
Asp Asp Leu Tyr Ile Lys Gly Ser Gly Ser Thr Ala Asn Leu Ala Ser
        275                 280                 285
Ser Asn Tyr Phe Pro Thr Pro Ser Gly Ser Met Val Thr Ser Asp Ala
    290                 295                 300
Gln Ile Phe Asn Lys Pro Tyr Trp Leu Gln Arg Ala Gln Gly His Asn
305                 310                 315                 320
Asn Gly Ile Cys Trp Gly Asn Gln Leu Phe Val Thr Val Val Asp Thr
                325                 330                 335
Thr Arg Ser Thr Asn Met Ser Leu Cys Ala Ala Ile Ser Thr Ser Glu
            340                 345                 350
Thr Thr Tyr Lys Asn Thr Asn Phe Lys Glu Tyr Leu Arg His Gly Glu
        355                 360                 365
Glu Tyr Asp Leu Gln Phe Ile Phe Gln Leu Cys Lys Ile Thr Leu Thr
    370                 375                 380
Ala Asp Val Met Thr Tyr Ile His Ser Met Asn Ser Thr Ile Leu Glu
385                 390                 395                 400
Asp Trp Asn Phe Gly Leu Gln Pro Pro Pro Gly Gly Thr Leu Glu Asp
                405                 410                 415
Thr Tyr Arg Phe Val Thr Ser Gln Ala Ile Ala Cys Gln Lys His Thr
            420                 425                 430
Pro Pro Ala Pro Lys Glu Asp Pro Leu Lys Lys Tyr Thr Phe Trp Glu
        435                 440                 445
Val Asn Leu Lys Glu Lys Phe Ser Ala Asp Leu Asp Gln Phe Pro Leu
    450                 455                 460
Gly Arg Lys Phe Leu Leu Gln Ala Gly Leu Lys Ala Lys Pro Lys Phe
465                 470                 475                 480
Thr Leu Gly Lys Arg Lys Ala Thr Pro Thr Thr Ser Ser Thr Ser Thr
                485                 490                 495
Thr Ala Lys Arg Lys Lys Arg Lys Leu
            500                 505
```

<210> SEQ ID NO 7
<211> LENGTH: 470
<212> TYPE: PRT
<213> ORGANISM: Artificial Sequence
<220> FEATURE:
<223> OTHER INFORMATION: HPV-16 L2 protein

<400> SEQUENCE: 7

```
Met Arg His Lys Arg Ser Ala Lys Arg Thr Lys Arg Ala Ser Ala Thr
 1               5                  10                  15

Gln Leu Tyr Lys Thr Cys Lys Gln Ala Gly Thr Cys Pro Pro Asp Ile
            20                  25                  30

Ile Pro Lys Val Glu Gly Lys Thr Ile Ala Asp Gln Ile Leu Gln Tyr
        35                  40                  45

Gly Ser Met Gly Val Phe Phe Gly Gly Leu Gly Ile Gly Thr Gly Ser
    50                  55                  60

Gly Thr Gly Gly Arg Thr Gly Tyr Ile Pro Leu Gly Thr Arg Pro Pro
65                  70                  75                  80

Thr Ala Thr Asp Thr Leu Ala Pro Val Arg Pro Pro Leu Thr Val Asp
                85                  90                  95

Pro Val Gly Pro Ser Asp Pro Ser Ile Val Ser Leu Val Glu Glu Thr
            100                 105                 110

Ser Phe Ile Asp Ala Gly Ala Pro Thr Ser Val Pro Ser Ile Pro Pro
        115                 120                 125

Asp Val Ser Gly Phe Ser Ile Thr Thr Ser Thr Asp Thr Thr Pro Ala
130                 135                 140

Ile Leu Asp Ile Asn Asn Thr Val Thr Thr Val Thr Thr His Asn Asn
145                 150                 155                 160

Pro Thr Phe Thr Asp Pro Ser Val Leu Gln Pro Pro Thr Pro Ala Glu
                165                 170                 175

Thr Gly Gly His Phe Thr Leu Ser Ser Ser Thr Ile Ser Thr His Asn
            180                 185                 190

Tyr Glu Glu Ile Pro Met Asp Thr Phe Ile Val Ser Thr Asn Pro Asn
        195                 200                 205

Thr Val Thr Ser Ser Thr Pro Ile Pro Gly Ser Arg Pro Val Ala Arg
    210                 215                 220

Leu Gly Leu Tyr Ser Arg Thr Thr Gln Gln Val Lys Val Val Asp Pro
225                 230                 235                 240

Ala Phe Val Thr Thr Pro Thr Lys Leu Ile Thr Tyr Asp Asn Pro Ala
                245                 250                 255

Tyr Glu Gly Ile Asp Val Asp Asn Thr Leu Tyr Phe Ser Ser Asn Asp
            260                 265                 270

Asn Ser Ile Asn Ile Ala Pro Asp Pro Asp Phe Leu Asp Ile Val Ala
        275                 280                 285

Leu His Arg Pro Ala Leu Thr Ser Arg Arg Thr Gly Ile Arg Tyr Ser
    290                 295                 300

Arg Ile Gly Asn Lys Gln Thr Leu Arg Thr Arg Ser Gly Lys Ser Ile
305                 310                 315                 320

Gly Ala Lys Val His Tyr Tyr Asp Phe Ser Thr Ile Asp Pro Ala
                325                 330                 335

Glu Glu Ile Glu Leu Gln Thr Ile Pro Ser Thr Tyr Thr Thr Thr
            340                 345                 350

Ser His Ala Ala Ser Pro Thr Ser Ile Asn Asn Gly Leu Tyr Asp Ile
        355                 360                 365
```

```
Tyr Ala Asp Asp Phe Ile Thr Asp Thr Ser Thr Thr Pro Val Pro Ser
        370                 375                 380

Val Pro Ser Thr Ser Leu Ser Gly Tyr Ile Pro Ala Asn Thr Thr Ile
385                 390                 395                 400

Pro Phe Gly Gly Ala Tyr Asn Ile Pro Leu Val Ser Gly Pro Asp Ile
            405                 410                 415

Pro Ile Asn Ile Thr Asp Gln Ala Pro Ser Leu Ile Pro Ile Val Pro
                420                 425                 430

Gly Ser Pro Gln Tyr Thr Ile Ile Ala Asp Ala Gly Asp Phe Tyr Leu
            435                 440                 445

His Pro Ser Tyr Tyr Met Leu Arg Lys Arg Arg Lys Arg Leu Pro Tyr
        450                 455                 460

Phe Phe Ser Asp Val Ser
465                 470

<210> SEQ ID NO 8
<211> LENGTH: 488
<212> TYPE: PRT
<213> ORGANISM: Artificial Sequence
<220> FEATURE:
<223> OTHER INFORMATION: HPV-16 L2/E7 fusion protein

<400> SEQUENCE: 8

Met Arg His Lys Arg Ser Ala Lys Arg Thr Lys Arg Ala Ser Ala Thr
 1               5                  10                  15

Gln Leu Tyr Lys Thr Cys Lys Gln Ala Gly Thr Cys Pro Pro Asp Ile
            20                  25                  30

Ile Pro Lys Val Glu Gly Lys Thr Ile Ala Asp Gln Ile Leu Gln Tyr
        35                  40                  45

Gly Ser Met Gly Val Phe Phe Gly Gly Leu Gly Ile Gly Thr Gly Ser
    50                  55                  60

Gly Thr Gly Gly Arg Thr Gly Tyr Ile Pro Leu Gly Thr Arg Pro Pro
65                  70                  75                  80

Thr Ala Thr Asp Thr Leu Ala Pro Val Arg Pro Pro Leu Thr Val Asp
                85                  90                  95

Pro Val Gly Pro Ser Asp Pro Ser Ile Val Ser Leu Val Glu Glu Thr
            100                 105                 110

Ser Phe Ile Asp Ala Gly Ala Pro Thr Pro Val Pro Ser Ile Pro Pro
        115                 120                 125

Asp Val Ser Gly Phe Ser Ile Thr Thr Ser Thr Asp Thr Thr Pro Ala
    130                 135                 140

Ile Leu Asp Ile Asn Asn Thr Val Thr Thr Val Thr Thr His Asn Asn
145                 150                 155                 160

Pro Thr Phe Thr Asp Pro Ser Val Leu Gln Pro Pro Thr Pro Ala Glu
                165                 170                 175

Thr Gly Gly His Phe Thr Leu Ser Ser Ser Thr Ile Ser Thr His Asn
            180                 185                 190

Tyr Glu Glu Ile Pro Met Asp Thr Phe Ile Val Ser Thr Asn Pro Asn
        195                 200                 205

Thr Val Thr Ser Ser Thr Pro Ile Pro Gly Ser Arg Pro Val Ala Arg
    210                 215                 220

Leu Gly Leu Tyr Ser Arg Thr Thr Gln Gln Val Lys Val Val Asp Pro
225                 230                 235                 240

Ala Phe Val Thr Thr Pro Thr Lys Leu Ile Thr Tyr Asp Asn Pro Ala
                245                 250                 255
```

-continued

```
Tyr Glu Gly Ile Asp Val Asp Asn Thr Leu Tyr Phe Pro Ser Asn Asp
            260                 265                 270

Asn Ser Ile Asn Ile Ala Pro Asp Pro Asp Phe Leu Asp Ile Val Ala
        275                 280                 285

Leu His Arg Pro Ala Leu Thr Ser Arg Arg Thr Gly Ile Arg Tyr Ser
    290                 295                 300

Arg Ile Gly Asn Lys Gln Thr Leu Arg Thr Arg Ser Gly Lys Ser Ile
305                 310                 315                 320

Gly Ala Lys Val His Tyr Tyr Asp Leu Ser Thr Ile Asn Pro Ala
                325                 330                 335

Glu Glu Ile Glu Leu Gln Thr Ile Thr Pro Ser Thr Tyr Thr Thr Pro
            340                 345                 350

Ser His Ala Ala Ser Pro Thr Ser Ile Asn Asn Gly Leu Tyr Asp Ile
        355                 360                 365

Tyr Ala Asp Asp Phe Ile Thr Asp Thr Phe Thr Thr Pro Val Pro Ser
    370                 375                 380

Ile Pro Ser Thr Ser Leu Ser Gly Tyr Ile Pro Ala Asn Thr Thr Ile
385                 390                 395                 400

Pro Phe Gly Gly Ala Tyr Asn Ile Pro Leu Val Ser Gly Pro Asp Ile
                405                 410                 415

Pro Ile Asn Thr Thr Asp Gln Thr Pro Ser Leu Ile Pro Ile Val Pro
            420                 425                 430

Gly Ser Pro Gln Tyr Thr Ile Ile Ala Asp Gly Gly Asp Phe Tyr Leu
        435                 440                 445

His Pro Ser Tyr Tyr Met Leu Arg Lys Arg Arg Lys Arg Leu Pro Tyr
    450                 455                 460

Phe Phe Ser Asp Val Ser Met His Gly Asp Thr Pro Thr Leu His Glu
465                 470                 475                 480

Tyr Met Leu Asp Leu Gln Pro Glu
                485

<210> SEQ ID NO 9
<211> LENGTH: 805
<212> TYPE: PRT
<213> ORGANISM: Artificial Sequence
<220> FEATURE:
<223> OTHER INFORMATION: HPV-16 L2/E7/E2 fusion protein

<400> SEQUENCE: 9

Met Arg His Lys Arg Ser Ala Lys Arg Thr Lys Arg Ala Ser Ala Thr
1               5                   10                  15

Gln Leu Tyr Lys Thr Cys Lys Gln Ala Gly Thr Cys Pro Pro Asp Ile
            20                  25                  30

Ile Pro Lys Val Glu Gly Lys Thr Ile Ala Asp Gln Ile Leu Gln Tyr
        35                  40                  45

Gly Ser Met Gly Val Phe Phe Gly Gly Leu Gly Ile Gly Thr Gly Ser
    50                  55                  60

Gly Thr Gly Gly Arg Thr Gly Tyr Ile Pro Leu Gly Thr Arg Pro Pro
65                  70                  75                  80

Thr Ala Thr Asp Thr Leu Ala Pro Val Arg Pro Pro Leu Thr Val Asp
                85                  90                  95

Pro Val Gly Pro Ser Asp Pro Ser Ile Val Ser Leu Val Glu Glu Thr
            100                 105                 110

Ser Phe Ile Asp Ala Gly Ala Pro Thr Ser Val Pro Ser Ile Pro Pro
        115                 120                 125
```

```
Asp Val Ser Gly Phe Ser Ile Thr Thr Ser Thr Asp Thr Thr Pro Ala
        130                 135                 140
Ile Leu Asp Ile Asn Asn Thr Val Thr Thr Val Thr Thr His Asn Asn
145                 150                 155                 160
Pro Thr Phe Thr Asp Pro Ser Val Leu Gln Pro Pro Thr Pro Ala Glu
                165                 170                 175
Thr Gly Gly His Phe Thr Leu Ser Ser Ser Thr Ile Ser Thr His Asn
            180                 185                 190
Tyr Glu Glu Ile Pro Met Asp Thr Phe Ile Val Ser Thr Asn Pro Asn
        195                 200                 205
Thr Val Thr Ser Ser Thr Pro Ile Pro Gly Ser Arg Pro Val Ala Arg
210                 215                 220
Leu Gly Leu Tyr Ser Arg Thr Gln Gln Val Lys Val Val Asp Pro
225                 230                 235                 240
Ala Phe Val Thr Thr Pro Thr Lys Leu Ile Thr Tyr Asp Asn Pro Ala
                245                 250                 255
Tyr Glu Gly Ile Asp Val Asp Asn Thr Leu Tyr Phe Ser Ser Asn Asp
            260                 265                 270
Asn Ser Ile Asn Ile Ala Pro Asp Pro Asp Phe Leu Asp Ile Val Ala
        275                 280                 285
Leu His Arg Pro Ala Leu Thr Ser Arg Arg Thr Gly Ile Arg Tyr Ser
290                 295                 300
Arg Ile Gly Asn Lys Gln Thr Leu Arg Thr Arg Ser Gly Lys Ser Ile
305                 310                 315                 320
Gly Ala Lys Val His Tyr Tyr Asp Phe Ser Ile Asp Pro Ala
                325                 330                 335
Glu Glu Ile Glu Leu Gln Thr Ile Thr Pro Ser Thr Tyr Thr Thr Thr
            340                 345                 350
Ser His Ala Ala Ser Pro Thr Ser Ile Asn Asn Gly Leu Tyr Asp Ile
        355                 360                 365
Tyr Ala Asp Asp Phe Ile Thr Asp Thr Ser Thr Thr Pro Val Pro Ser
        370                 375                 380
Val Pro Ser Thr Ser Leu Ser Gly Tyr Ile Pro Ala Asn Thr Thr Ile
385                 390                 395                 400
Pro Phe Gly Gly Ala Tyr Asn Ile Pro Leu Val Ser Gly Pro Asp Ile
                405                 410                 415
Pro Ile Asn Ile Thr Asp Gln Ala Pro Ser Leu Ile Pro Ile Val Pro
            420                 425                 430
Gly Ser Pro Gln Tyr Thr Ile Ile Ala Asp Ala Gly Asp Phe Tyr Leu
        435                 440                 445
His Pro Ser Tyr Tyr Met Leu Arg Lys Arg Arg Lys Arg Leu Pro Tyr
        450                 455                 460
Phe Phe Ser Asp Val Ser Met His Gly Asp Thr Pro Thr Leu His Glu
465                 470                 475                 480
Tyr Met Leu Asp Leu Gln Pro Glu Thr Thr Asp Leu Tyr Gly Tyr Glu
                485                 490                 495
Gln Leu Asn Asp Ser Ser Glu Glu Asp Glu Ile Asp Gly Pro Ala
            500                 505                 510
Gly Gln Ala Glu Pro Asp Arg Ala His Tyr Asn Ile Val Thr Phe Cys
        515                 520                 525
Cys Lys Cys Asp Ser Thr Leu Arg Leu Cys Val Gln Ser Thr His Val
        530                 535                 540
Asp Ile Arg Thr Leu Glu Asp Leu Leu Met Gly Thr Leu Gly Ile Val
```

-continued

```
                545                 550                 555                 560

Cys Pro Ile Cys Ser Gln Lys Pro Ser Met Glu Thr Leu Cys Gln Arg
                565                 570                 575

Leu Asn Val Cys Gln Asp Lys Ile Leu Thr His Tyr Glu Asn Asp Ser
                580                 585                 590

Thr Asp Leu Arg Asp His Ile Asp Tyr Trp Lys His Met Arg Leu Glu
                595                 600                 605

Cys Ala Ile Tyr Tyr Lys Ala Arg Glu Met Gly Phe Lys His Ile Asn
                610                 615                 620

His Gln Val Val Pro Thr Leu Ala Val Ser Lys Asn Lys Ala Leu Gln
625                 630                 635                 640

Ala Ile Glu Leu Gln Leu Thr Leu Glu Thr Ile Tyr Asn Ser Gln Tyr
                645                 650                 655

Ser Asn Glu Lys Trp Thr Leu Gln Asp Val Ser Leu Glu Val Tyr Leu
                660                 665                 670

Thr Ala Pro Thr Gly Cys Ile Lys Lys His Gly Tyr Thr Val Glu Val
                675                 680                 685

Gln Phe Asp Gly Asp Ile Cys Asn Thr Met His Tyr Thr Asn Trp Thr
690                 695                 700

His Ile Tyr Ile Cys Glu Ala Ser Val Thr Val Val Glu Gly Gln
705                 710                 715                 720

Val Asp Tyr Tyr Gly Leu Tyr Tyr Val His Glu Gly Ile Arg Thr Tyr
                725                 730                 735

Phe Val Gln Phe Lys Asp Asp Ala Glu Lys Tyr Ser Lys Asn Lys Val
                740                 745                 750

Trp Glu Val His Ala Gly Gly Gln Val Ile Leu Cys Pro Thr Ser Val
                755                 760                 765

Phe Ser Ser Asn Glu Val Ser Ser Pro Glu Ile Ile Arg Gln His Leu
                770                 775                 780

Ala Asn His Ser Ala Ala Thr His Thr Lys Ala Val Ala Leu Gly Thr
785                 790                 795                 800

Glu Glu Thr Gln Thr
                805
```

<210> SEQ ID NO 10
<211> LENGTH: 536
<212> TYPE: PRT
<213> ORGANISM: Artificial Sequence
<220> FEATURE:
<223> OTHER INFORMATION: HPV-16 L2/E6 fusion protein

<400> SEQUENCE: 10

```
Met Arg His Lys Arg Ser Ala Lys Arg Thr Lys Arg Ala Ser Ala Thr
1               5                   10                  15

Gln Leu Tyr Lys Thr Cys Lys Gln Ala Gly Thr Cys Pro Pro Asp Ile
                20                  25                  30

Ile Pro Lys Val Glu Gly Lys Thr Ile Ala Asp Gln Ile Leu Gln Tyr
                35                  40                  45

Gly Ser Met Gly Val Phe Phe Gly Gly Leu Gly Ile Gly Thr Gly Ser
                50                  55                  60

Gly Thr Gly Gly Arg Thr Gly Tyr Ile Pro Leu Gly Thr Arg Pro Pro
65                  70                  75                  80

Thr Ala Thr Asp Thr Leu Ala Pro Val Arg Pro Pro Leu Thr Val Asp
                85                  90                  95

Pro Val Gly Pro Ser Asp Pro Ser Ile Val Ser Leu Val Glu Glu Thr
```

-continued

```
                100                 105                 110
Ser Phe Ile Asp Ala Gly Ala Pro Thr Ser Val Pro Ser Ile Pro Pro
            115                 120                 125

Asp Val Ser Gly Phe Ser Ile Thr Thr Ser Thr Asp Thr Thr Pro Ala
            130                 135                 140

Ile Leu Asp Ile Asn Asn Thr Val Thr Thr Val Thr Thr His Asn Asn
145                 150                 155                 160

Pro Thr Phe Thr Asp Pro Ser Val Leu Gln Pro Pro Thr Pro Ala Glu
            165                 170                 175

Thr Gly Gly His Phe Thr Leu Ser Ser Ser Thr Ile Ser Thr His Asn
            180                 185                 190

Tyr Glu Glu Ile Pro Met Asp Thr Phe Ile Val Ser Thr Asn Pro Asn
            195                 200                 205

Thr Val Thr Ser Ser Thr Pro Ile Pro Gly Ser Arg Pro Val Ala Arg
210                 215                 220

Leu Gly Leu Tyr Ser Arg Thr Thr Gln Gln Val Lys Val Val Asp Pro
225                 230                 235                 240

Ala Phe Val Thr Thr Pro Thr Lys Leu Ile Thr Tyr Asp Asn Pro Ala
            245                 250                 255

Tyr Glu Gly Ile Asp Val Asp Asn Thr Leu Tyr Phe Ser Ser Asn Asp
            260                 265                 270

Asn Ser Ile Asn Ile Ala Pro Asp Pro Asp Phe Leu Asp Ile Val Ala
            275                 280                 285

Leu His Arg Pro Ala Leu Thr Ser Arg Arg Thr Gly Ile Arg Tyr Ser
            290                 295                 300

Arg Ile Gly Asn Lys Gln Thr Leu Arg Thr Arg Ser Gly Lys Ser Ile
305                 310                 315                 320

Gly Ala Lys Val His Tyr Tyr Asp Phe Ser Thr Ile Asp Pro Ala
            325                 330                 335

Glu Glu Ile Glu Leu Gln Thr Ile Thr Pro Ser Thr Tyr Thr Thr Thr
            340                 345                 350

Ser His Ala Ala Ser Pro Thr Ser Ile Asn Asn Gly Leu Tyr Asp Ile
            355                 360                 365

Tyr Ala Asp Asp Phe Ile Thr Asp Thr Ser Thr Thr Pro Val Pro Ser
            370                 375                 380

Val Pro Ser Thr Ser Leu Ser Gly Tyr Ile Pro Ala Asn Thr Thr Ile
385                 390                 395                 400

Pro Phe Gly Gly Ala Tyr Asn Ile Pro Leu Val Ser Gly Pro Asp Ile
            405                 410                 415

Pro Ile Asn Ile Thr Asp Gln Ala Pro Ser Leu Ile Pro Ile Val Pro
            420                 425                 430

Gly Ser Pro Gln Tyr Thr Ile Ile Ala Asp Ala Gly Asp Phe Tyr Leu
            435                 440                 445

His Pro Ser Tyr Tyr Met Leu Arg Lys Arg Lys Arg Leu Pro Tyr
            450                 455                 460

Phe Phe Ser Asp Val Ser Met His Gln Lys Arg Thr Ala Met Phe Gln
465                 470                 475                 480

Asp Pro Gln Glu Arg Pro Arg Lys Leu Pro Gln Leu Cys Thr Glu Leu
            485                 490                 495

Gln Thr Thr Ile His Asp Ile Ile Leu Glu Cys Val Tyr Cys Lys Gln
            500                 505                 510

Gln Leu Leu Arg Arg Glu Val Tyr Asp Phe Ala Phe Arg Asp Leu Cys
            515                 520                 525
```

Ile Val Tyr Arg Asp Gly Asn Pro
    530             535

<210> SEQ ID NO 11
<211> LENGTH: 1518
<212> TYPE: DNA
<213> ORGANISM: Artificial Sequence
<220> FEATURE:
<223> OTHER INFORMATION: HPV-16 L1 wild type NVAX clone

<400> SEQUENCE: 11

| | |
|---|---|
| atgtctcttt ggctgcctag tgaggccact gtctacttgc ctcctgtccc agtatctaag | 60 |
| gttgtaagca cggatgaata tgttgcacgc acaaacatat attatcatgc aggaacatcc | 120 |
| agactacttg cagttggaca tcccTATTTT cctattaaaa acctaacaa taacaaaata | 180 |
| ttagttccta agtatcagg attacaatac agggtattta gaatacattt acctgacccc | 240 |
| aataagtttg gttttcctga cacctcattt tataatccag atacacagcg gctggtttgg | 300 |
| gcctgtgtag gtgttgaggt aggtcgtggt cagccattag gtgtgggcat tagtggccat | 360 |
| cctttattaa ataaattgga tgacacagaa atgctagtg cttatgcagc aaatgcaggt | 420 |
| gtggataata gagaatgtat atctatggat tacaaacaaa cacaattgtg tttaattggt | 480 |
| tgcaaaccac ctataggga acactggggc aaggatccc catgtaccaa tgttgcagta | 540 |
| aatccaggtg attgtccacc attagagtta ataaacacag ttattcagga tggtgatatg | 600 |
| gttgatactg ctttggtgc tatggacttt actacattac aggctaacaa agtgaagtt | 660 |
| ccactggata tttgtacatc tatttgcaaa tatccagatt atattaaaat ggtgtcagaa | 720 |
| ccatatggcg acagcttatt tttttattta cgaagggaac aaatgtttgt tagacattta | 780 |
| tttaataggg ctggtgctgt tggtgaaaat gtaccagacg atttatacat taaaggctct | 840 |
| gggtctactg caaatttagc cagttcaaat tattttccta cacctagtgg ttctatggtt | 900 |
| acctctgatg cccaaatatt caataaacct tattggttac aacgagcaca gggccacaat | 960 |
| aatggcattt gttgggggtaa ccaactattt gttactgttg ttgatactac acgcagtaca | 1020 |
| aatatgtcat tatgtgctgc catatctact tcagaaacta catataaaaa tactaacttt | 1080 |
| aaggagtacc tacgacatgg ggaggaatat gatttacagt ttatttttca actgtgcaaa | 1140 |
| ataaccttaa ctgcagacgt tatgacatac atacattcta tgaattccac tatttttgga | 1200 |
| gactggaatt ttggtctaca acctccccca ggaggcacac tagaagatac ttataggttt | 1260 |
| gtaacatccc aggcaattgc ttgtcaaaaa catacacctc cagcacctaa agaagatccc | 1320 |
| cttaaaaaat acacttttg ggaagtaaat ttaaaggaaa agtttctgc agacctagat | 1380 |
| cagtttcctt taggacgcaa attttactta caagcaggat gaaggccaa accaaaattt | 1440 |
| acattaggaa aacgaaaagc tacacccacc acctcatcta cctctacaac tgctaaacgc | 1500 |
| aaaaaacgta agctgtaa | 1518 |

<210> SEQ ID NO 12
<211> LENGTH: 1518
<212> TYPE: DNA
<213> ORGANISM: Artificial Sequence
<220> FEATURE:
<223> OTHER INFORMATION: HPV-16 L1 wild type clone (GenBank K02718)

<400> SEQUENCE: 12

| | |
|---|---|
| atgtctcttt ggctgcctag tgaggccact gtctacttgc ctcctgtccc agtatctaag | 60 |
| gttgtaagca cggatgaata tgttgcacgc acaaacatat attatcatgc aggaacatcc | 120 |

```
agactacttg cagttggaca tccctatttt cctattaaaa aacctaacaa taacaaaata      180
ttagttccta aagtatcagg attacaatac agggtattta gaatacattt acctgacccc      240
aataagtttg ttttcctga cacctcattt tataatccag atacacagcg gctggtttgg       300
gcctgtgtag gtgttgaggt aggtcgtggt cagccattag gtgtgggcat tagtggccat      360
cctttattaa ataaattgga tgacacagaa atgctagtg cttatgcagc aaatgcaggt       420
gtggataata gagaatgtat atctatggat tacaaacaaa cacaattgtg tttaattggt      480
tgcaaaccac ctataggga acactggggc aaaggatccc catgtaccaa tgttgcagta      540
aatccaggtg attgtccacc attagagtta ataaacacag ttattcagga tggtgatatg      600
gttcatactg gctttggtgc tatggacttt actacattac aggctaacaa agtgaagtt     660 ccactggata tttgtacatc tatttgcaaa tatccagatt atattaaaat ggtgtcagaa      720
ccatatggcg acagcttatt ttttattta cgaagggaac aaatgtttgt tagacattta      780
tttaataggg ctggtactgt tggtgaaaat gtaccagacg atttatacat taaaggctct      840
gggtctactg caaatttagc cagttcaaat tattttccta cacctagtgg ttctatggtt      900
acctctgatg cccaaatatt caataaaacct tattggttac aacgagcaca gggccacaat      960
aatggcattt gttgggtaa ccaactattt gttactgttg ttgatactac acgcagtaca      1020
aatatgtcat tatgtgctgc catatctact tcagaaacta catataaaaa tactaacttt      1080
aaggagtacc tacgcatgg ggaggaatat gatttacagt ttatttttca actgtgcaaa      1140
ataaccttaa ctgcagacgt tatgacatac atacattcta tgaattccac tattttggag      1200
gactggaatt ttggtctaca acctccccca ggaggcacac tagaagatac ttataggttt      1260
gtaacccagg caattgcttg tcaaaaacat acacctccag cacctaaaga agatgatccc      1320
cttaaaaaat acacttttg ggaagtaaat ttaaaggaaa agttttctgc agacctagat      1380
cagtttcctt taggacgcaa attttttacta caagcaggat tgaaggccaa accaaaattt      1440
acattaggaa acgaaaagc tacacccacc acctcatcta cctctacaac tgctaaacgc      1500 aaaaacgta agctgtaa                                                   1518

<210> SEQ ID NO 13
<211> LENGTH: 1413
<212> TYPE: DNA
<213> ORGANISM: Artificial Sequence
<220> FEATURE:
<223> OTHER INFORMATION: HPV-16 L2 wild type NVAX clone

<400> SEQUENCE: 13
atgcgacaca acgttctgc aaaacgcaca aacgtgcat cggctaccca actttataaa       60
acatgcaaac aggcaggtac atgtccacct gacattatac ctaaggttga aggcaaaact      120
attgctgatc aaatattaca atatggaagt atgggtgtat tttttggtgg gttaggaatt      180
ggaacagggt cgggtacagg cggacgcact gggtatattc cattgggaac aaggcctccc      240
acagctacag atacacttgc tcctgtaaga ccccctttaa cagtagatcc tgtgggccct      300 tctgatccttt ctatagtttc tttagtggaa gaaactagtt ttattgatgc tggtgcacca      360
acatctgtac cttccattcc cccagatgta tcaggattta gtattactac ttcaactgat      420
accacacctg ctatattaga tattaataat actgttacta ctgttactac acataataat      480
cccactttca ctgacccatc tgtattgcag cctccaacac ctgcagaaac tggagggcat      540
tttacacttt catcatccac tattagtaca cataattatg aagaaattcc tatggataca      600
```

```
                                                              -continued
tttattgtta gcacaaaccc taacacagta actagtagca cacccatacc agggtctcgc        660
ccagtggcac gcctaggatt atatagtcgc acaacacaac aagttaaagt tgtagaccct        720
gcttttgtaa ccactcccac taaacttatt acatatgata atcctgcata tgaaggtata        780
gatgtggata atacattata tttttctagt aatgataata gtattaatat agctccagat        840
cctgactttt tggatatagt tgctttacat aggccagcat taacctctag gcgtactggc        900
ataaggtaca gtagaattgg taataaacaa acactacgta ctcgtagtgg aaaatctata        960
ggtgctaagg tacattatta ttatgatttt agtaccattg atcctgcaga agaaatagaa       1020
ttacaaacta taacaccttc tacatatact accacttcac atgcagcctc acctacttct       1080
attaataatg gattatatga tatttatgca gatgacttta ttacagatac ttctacaacc       1140
ccggtaccat ctgtaccctc tacatcttta tcaggttata ttcctgcaaa tacaacaatt       1200 cctttggtg gtgcatacaa tattccttta gtatcaggtc ctgatatacc cattaatata       1260
actgaccaag ctccttcatt aattcctata gttccagggt ctccacaata tacaattatt       1320
gctgatgcag gtgacttta tttacatcct agttattaca tgttacgaaa acgacgtaaa       1380
cgtttaccat attttttttc agatgtatcc tga                                    1413
```

INSECT CELL LINE

CROSS REFERENCE TO RELATED APPLICATIONS

This application claims benefit under 37 U.S.C. §119(e) based on U.S. Provisional Application Nos. 60/356,119, 60/356,161, 60/356,118, 60/356,133, 60/356,157, 60/356,156, 60/356,123, 60/356,113, 60/356,154, 60/356,135, 60/356,126, 60/356,162, 60/356,150, 60/356,151 and 60/356,152, each filed Feb. 14, 2002, the entire contents of each of which are incorporated herein by reference.

FIELD OF THE INVENTION

The present invention relates generally to clonal selection processes of insect cells for enhanced foreign gene expression from recombinant baculoviruses.

BACKGROUND OF THE INVENTION

Insect cell lines are used as a culture system for the production of diagnostics and vaccines used in human and veterinary medicine. Many recombinant proteins have been expressed in insect cells that are immunogenically, antigenically, and functionally similar to the native proteins. The desired product is an expressed protein that is produced in large amounts and that is as similar to the natural protein as possible, including necessary post-translation processing and modification. Among the post-translational processing steps that have been shown to occur in insect cells are fatty acid acylation, phosphorylation, and glycosylation (Luckow, V. A. 1995. In: Baculoviruses Expression Systems and Biopesticides, Shuler et al., Eds. Wiley-Liss, New York, N. Y., pages 51–90). Most of the proteins recovered from insect cell cultures, however, migrated faster on SDS-PAGE gels than the native protein, indicating a lower molecular weight because of incomplete post-translational modification.

Baculoviruses as expression vectors are used to produce large amounts of recombinant proteins of medical, pharmaceutical, and veterinary importance in various insect cell lines. Differences in yields of expressed gene products from engineered baculoviruses among cell lines have been reported. Hink et al. (1991) *Biotechnol Prog.* 7:9–14, compared the expression of three recombinant proteins in twenty-three different cell lines. For each protein, the yield varied among the cell lines and no single cell line produced the highest yields for all three proteins.

In order to facilitate downstream recovery and purification of the expressed recombinant proteins and to reduce costs, insects cells are grown in suspension in large volumes and in medium free of fetal bovine serum (FBS) (Vaughn, J. 1999), In: *Encyclopedia of Bioprocess Technology: Fermentation, Biocatalysis, and Bioseparation*, Flickinger et al., Eds. John Wiley & Sons, Inc., NY, pages 1444–1457). There are several protein-free media available from commercial suppliers and the yields of recombinant gene products from cells grown in these media generally have been comparable to yields in FBS-supplemented media.

Yields of protein from baculovirus expression vectors in insect cell cultures are reported to be many times higher than those from mammalian cells. The baculovirus expression vector system (BEVS) has been used with hundreds of genes, the majority of which have expressed biologically active proteins (Vaughn, J., supra). The majority of the host cell lines, however, express the recombinant gene products intracellularly. There exists a need in the art for new cell lines that express recombinant gene products extracellularly, and to produce high yields of functional proteins with the desired post-translation modification and proper protein folding.

The invention, as disclosed and described herein, overcomes the shortcomings of the prior art recombinant protein production through the generation of novel insect cell lines that express post translationally modified recombinant proteins extracellularly. The use of the novel cell lines of the invention results in the enhanced expression of expressed recombinant proteins that demonstrate enhanced antigenicity and immunogenicity.

SUMMARY OF THE INVENTION

The present invention relates to a novel cell line that is generated through clonal selection and propagation of insect cells of the lepidopteran family. The invention further relates to the use of this novel cell line to express a wide range of recombinant proteins with an enhanced yield. In particular, the novel cell line of the invention is used to express recombinant viral coat proteins that self-assemble into virus-like particles (VLPs). The recombinant viral proteins are preferably expressed extracellularly.

Accordingly, in one aspect of the present invention a cell line designated ATCC PTA-4047 is provided.

According to one embodiment of the invention, there is provided a cell that is a clone, derivative, mutant, and/or transfectant of the cell line designated ATCC PTA-4047, wherein the cell upon culture grows continuously and retains the identifying characteristics of the cell line designated ATCC-PTA 4047.

According to another aspect of the invention, there is provided a line of Sf-9S cells exhibiting at least one of the following characteristics: (a) expresses recombinant gene products extracellularly after infection by a recombinant baculovirus; (b) grows in suspension or shaker flask cell culture; (c) grows in serum-free medium; and (e) supports replication of the recombinant baculovirus in the serum free medium.

In one embodiment, the transformed Sf-9S cells express recombinant viral gene products. In a preferred embodiment, the recombinant viral gene products are viral capsid proteins that self assemble into virus-like particles. The virus-like particles are virus-like particles of an enveloped virus, a non-enveloped virus, or both. The enveloped and non-enveloped viruses include, for example, rotavirus, calicivirus, papillomavirus, hepatitis C virus, hepatitis E virus, influenza virus, human immunodeficiency virus, or a combination thereof. In a preferred embodiment, the virus-like particles are derived from a non-enveloped virus such as human papillomavirus (HPV).

According to another embodiment, the virus-like particles of HPV are encoded by codon optimized HPV L1 or HPV chimeric polynucleotides comprising SEQ ID NO. 1, SEQ ID NO. 2, SEQ ID NO. 3, SEQ ID NO. 4, and SEQ ID NO. 5, or a polynucleotide having a sequence that is substantially homologous to any one of the SEQ ID NO. 1, SEQ ID NO. 2, SEQ ID NO. 3, SEQ ID NO. 4, and SEQ ID NO. 5.

In yet another aspect, the invention provides a process for producing a cell line, comprising one or more of the following steps: (a) weaning at least one cell from serum dependency to growth in a substantially serum-free medium, the weaning comprises: (1) plating a plurality of cells in plurality of wells containing serum-containing media, wherein a single cell is plated in each well; (2) identifying the well with replicating cells, (3) culturing the replicating cells into replica-plating wells; (4) changing the medium in each identified well with replicating cells; (5) increasing the proportion of serum-free medium as compared to serum-containing medium; (6) repeating the identifying and medium changing steps until the medium in each well comprises substantially serum-free medium; (7) harvesting the cells from each well containing the substantially serum-free-medium; wherein if the harvested cells reached a predetermined density they are designated as the serum-weaned cells; and (8) culturing the serum weaned cells; (b) selecting at least one of the serum-weaned cells capable of growth as a single-cell suspension in the substantially serum-free medium; and (c) passaging at least one selected serum-weaned cell to establish the cell line.

In yet another embodiment, the process further comprises one or more of the following steps: (d) plating at least one of the serum-weaned cells, each serum-weaned cell plated in a separate well; (e) selecting each well with a single serum-weaned cell; (f) culturing the single serum-weaned cell in each selected well; (g) identifying each selected well with replicating serum-weaned cells; (h) culturing the replicating serum-weaned cells into at least one replica-plating well; (i) infecting at least one of the replica-plated cells with a first recombinant baculovirus expressing a viral capsid protein that self-assemble into first virus-like particles; (j) measuring the extracellular amount of the first virus-like particles in the at least one replica-plating well; and if the extracellular amount of the first virus-like particles exceeds a first predetermined level, selecting the infected cells as Sf-9S transformed cells.

In a preferred embodiment, the process further comprises one or more of the following steps: (k) replica-plating the selected infected cells of step (j) into at least one replica-plating well; (l) infecting at least one of the replica-plated selected infected cells with a second recombinant baculovirus expressing viral capsid proteins that self-assemble into second virus-like particles; and (m) measuring the extracellular amount of the second virus-like particles in the at least one replica-plated well; wherein if the measured extracellular amount of the second virus-like particles exceeds a second predetermined level, designating the replica-plated selected infected cells as Sf-9S transformed cells.

BRIEF DESCRIPTION OF THE FIGURES

Figure 1A:
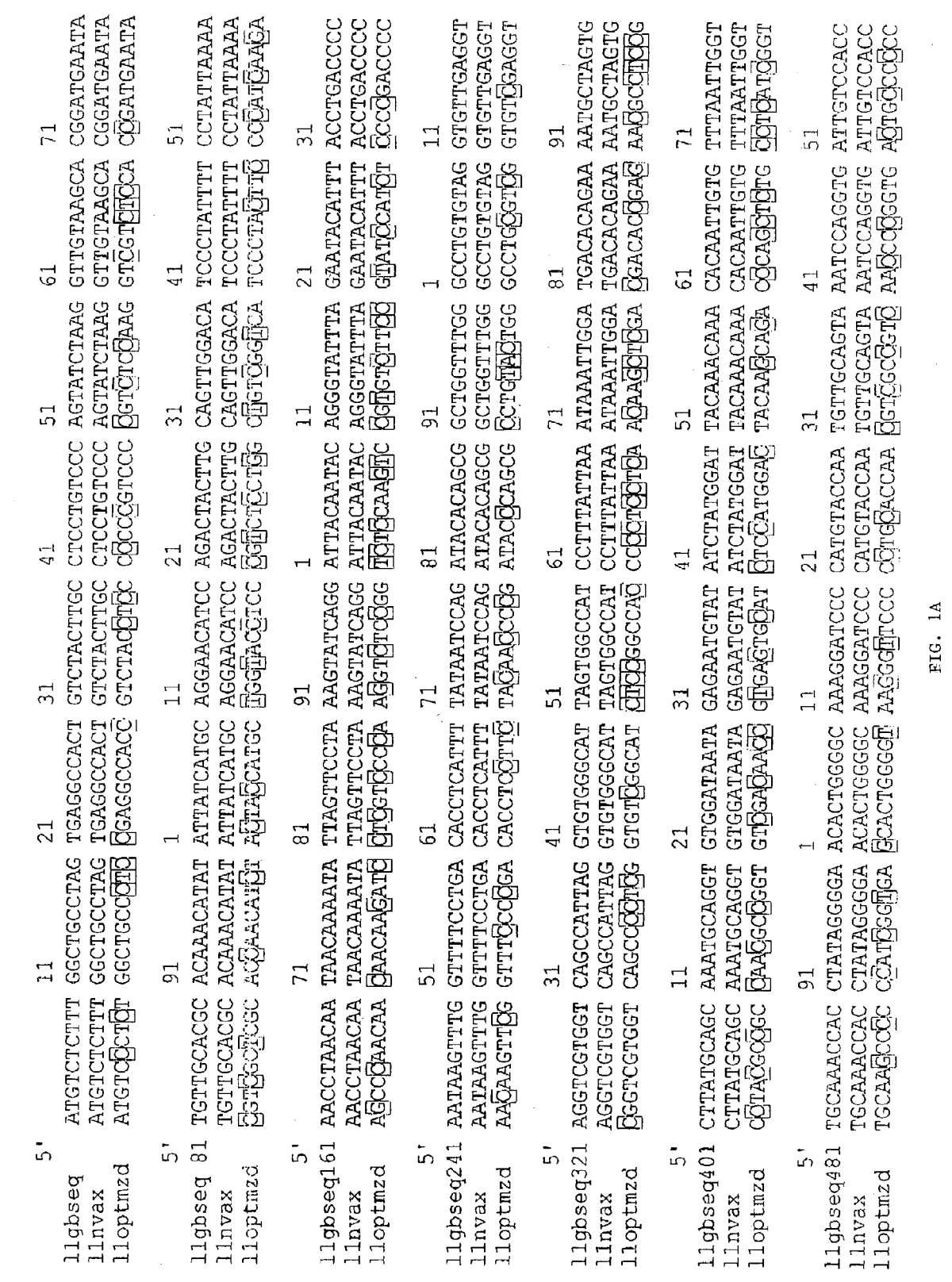
Figure 1B:
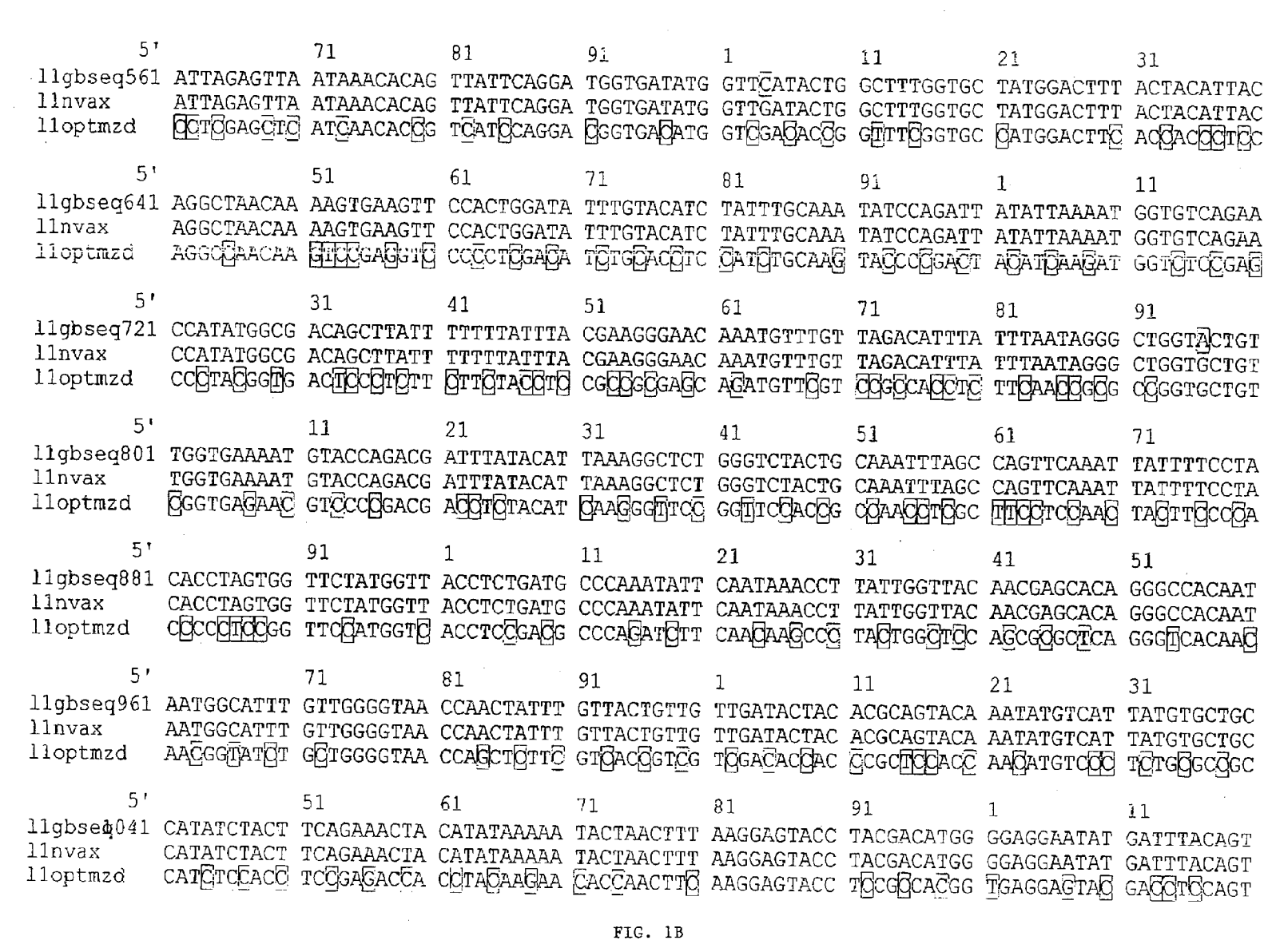

FIGS. 1A–1C show the alignment of two wild-type HPV-16 papilloma virus L1 polynucleotide sequences with a codon-optimized HPV-16 L1 polynucleotide of the invention. The aligned sequences are: HPV-16 L1 wild-type sequence from GenBank record Accession No. K0278 ("11gbseq"; SEQ ID No. 12), HPV-16 wild type clone NVAX ("11nvax", SEQ ID No. 11), and HPV-16 codon-optimized L1 ("11optmzd"; SEQ ID No. 1). The sequences were aligned using the Gene Runner™ program (Hastings Software) available through the website maintained by the National Center for Biotechnology Information (NCBI). Nucleotides which differ between the aligned sequences are boxed.

FIG. 10A shows proteins detected chromogenically on membranes by Western blot analysis of recombinant HPV-16 L1 VLPs purified according to the methods of the present invention and bound to polyclonal antisera to AcMNPV wild-type baculovirus (1:500).

DETAILED DESCRIPTION OF THE INVENTION

Figure 2:
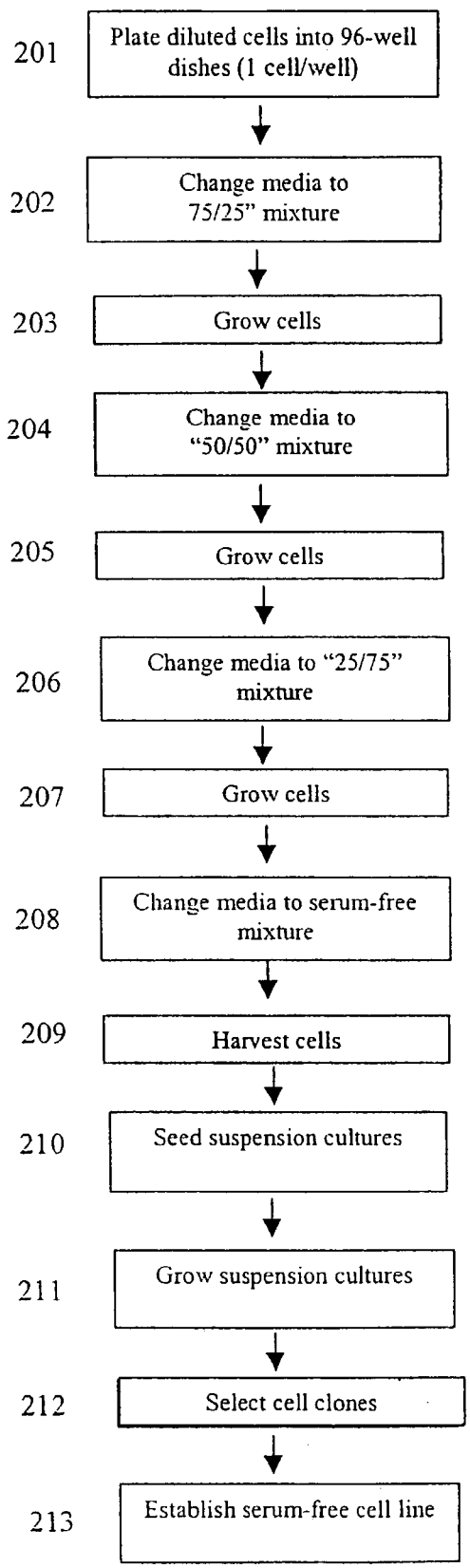
FIG. 2 shows a schematic flowchart of the steps in the weaning selection process of an insect cell line capable of growing in serum-free media as suspension cell cultures.

The invention, as disclosed and described herein, provides a novel insect cell line for the production of recombinant gene products. The cell line of the invention is a stable cell lines that grows in the absence of serum in the media. Cell lines that grow in serum free media are more compliant with regulatory requirements for pharmaceuticals, are less likely to be infected by bovine spongiform encephalitis virus, and are chemically defined.

Definitions

The definitions used in this application are for illustrative purposes and do not limit the scope of the invention.

As used in herein, "virus-like particles" or "VLPs" refers to virus particles that self-assemble into intact virus structures comprised of capsid proteins such as papillomavirus L1 capsid proteins. VLPs are morphologically and antigenically similar to authentic virions, but do not contain genetic information sufficient to replicate and thus are non-infectious. VLPs are produced in suitable host cells (i.e. yeast, mammalian, and insect host cells), wherein upon isolation and further purification under suitable conditions are purified as intact VLPs.

As used herein, "chimeric VLP" refers to recombinant papillomavirus L1 capsid protein, or peptide fragment thereof, that encapsulates other papillomavirus gene products or heterologous gene products during self-assembly into virus-like particles. For example, gene products containing the HPV L2, E2, E6, and/or E7 and which become encapsulated into the HPV L1 VLPs are considered herein as chimeric VLPs.

As used herein, "L2 fusion protein" refers to a protein, or a peptide fragment thereof, encoded by a papillomavirus L2 scaffolding gene fused to papillomavirus or other viral genes including heterologous gene(s).

As used herein, "heterologous viral capsid genes" refers to viral genes encoding the major structural virion component from different viruses, for example, the rotavirus VP2, VP6, HPV-16 L2, and HPV-16 L1 genes.

As used herein, "protein" is used interchangeably with polypeptide, peptide and peptide fragments.

As used herein, "polynucleotide" includes cDNA, RNA, DNA/RNA hybrid, anti-sense RNA, ribozyme, genomic DNA, synthetic forms, and mixed polymers, both sense and antisense strands, and may be chemically or biochemically modified to contain non-natural or derivatized, synthetic, or semi-synthetic nucleotide bases. Also, included within the scope of the invention are alterations of a wild type or synthetic gene, including but not limited to deletion, insertion, substitution of one or more nucleotides, or fusion to other polynucleotide sequences, provided that such changes in the primary sequence of the gene do not alter the expressed peptide ability to elicit protective immunity.

As used herein, "transformed cells" refer to cells that express one or more recombinant gene products transiently or stably.

As used herein, "gene products" include any product that is produced in the course of the transcription, reverse-transcription, polymerization, translation, post-translation and/or expression of a nucleotide molecule. Gene products include, but are not limited to, proteins, polypeptides, peptides, or peptide fragments.

As used herein, "L1 protein" refers to the structural protein of papillomavirus L1 capsid genes and constitutes the major portion of the papillomavirus ("PV") capsid structure. This protein has reported application in the preparation of HPV vaccines and diagnostic reagents.

As used herein, "L2 protein" refers to the structural scaffolding protein of papillomavirus, which constitutes a minor portion of the papillomavirus capsid structure and facilitates the assembly of papillomavirus particles within cell nuclei.

As used herein, "L2/E7 protein" refers to a fusion protein, or a fragment thereof, encoded by a papillomavirus L2 scaffolding gene fused to a papillomavirus E7 transforming gene that may have one or more mutations.

As used herein, "L2/E7/E2 protein" refers to a fusion protein, or a fragment thereof, encoded by a papillomavirus L2 scaffolding gene fused to (a) papillomavirus E2 transactivation gene that may have mutations and (b) a papillomavirus E7 transforming gene. The fused gene includes one or more mutated genes.

As used herein, "L2/E6 protein" refers to a fusion protein, or a peptide fragment thereof, encoded by a papillomavirus L2 scaffolding gene fused to a papillomavirus E6 transforming gene that may have one or more mutations.

As disclosed herein, "mutation" includes substitutions, transversions, transitions, transpositions, reversions, deletions, insertions, or other events that may have improved desired activity, or a decreased undesirable activity of the gene. Mutation encompasses null mutations in natural virus isolates or in synthesized genes that may change the primary amino acid sequences of the expressed protein but do not affect self-assembly of capsid proteins, and antigenicity or immunogenicity of VLPs or chimeric VLPs.

As disclosed herein, "substantially homologous sequences" include those sequences which have at least about 50% homology, preferably at least about 60–70%, more preferably at least about 70–80% homology and most preferably at least about 95% or more homology to the codon optimized polynucleotides of the invention.

1. Novel Cell Line 1.1 Sf-9S cell line

According to one aspect of the invention described herein, there is provided a novel cell line designated as Sf-9S, which was deposited as cell line ATCC PTA-4047 on Feb. 4, 2002, under the Budapest Treaty, with the American Type Culture Collection (ATCC), located at 10801 University Boulevard, Manassas, Va. 20110. The Sf-9S cell line is derived from the parent S. frugiperda Sf-9 cell line (ATCC CRL-1771) and established by clonal selection based on serum-independent growth. This cell line is used as a host cell substrate in a single cell suspension maintained at a large manufacturing scale. The Sf-9S cell line of the invention is capable of enhanced expression of recombinant gene products. The designations "Sf-9S" and "ATCC PTA-4047" are used herein interchangeably, and refer to the same cell line.

According to one embodiment of the invention, there is provided a process for developing cell lines from the parent cell line Sf-9S. The first step of this process involves progressive weaning of cells from serum-containing media to serum-free media. Master and working cell banks of the cell line are constructed and qualified according to safety, identity, and biological criteria or specifications. Prior to commencement of the clonal selection process, master and working cell banks of the parental cell line Sf-9 cells are cultivated as monolayer cultures for at least 10, preferably at least 20, and more preferably at least 30 passages in Grace's insect media (Life Technologies, Grand Island, N.Y. 14072) supplemented with 10% fetal bovine serum (Life Technologies, Grand Island, N.Y. 14072). A master cell bank of Sf-9 cells is stored in conditioned serum-containing media at −70° C. and in liquid nitrogen. A working cell bank is established from a single cryovial of the Sf-9 master cell bank and cultivated in serum-containing insect media for multiple cell passages. The clonal selection process, according to the invention, includes several rounds as demonstrated in FIG. 2.

The method of clonal selection according to the invention described herein includes generally weaning a plurality of cells from serum-dependence to obtain at least one cell that can grow in serum-free medium.

According to another aspect, the invention provides a process for producing a cell line comprising one or more of the following steps: (a) plating a plurality of cells in wells containing serum-containing medium, one cell per well; (b) culturing the cell in each separate well; (c) identifying each well with replicating cells; (d) culturing the replicating cells into replica-plating wells; (e) changing the medium in each identified well with replicating cells by increasing the proportion of serum-free medium to serum-containing medium; (f) repeating identifying, culturing, and medium-changing of steps (c)–(e) until the medium for each well is approximately 100% serum-free; (g) harvesting the cells from each serum-free well; and (h) culturing the harvested cells in suspension. Suspension cultures of harvested cells that grow to a predetermined cell density for multiple passages are designated serum-free cell clones.

According to another embodiment, the method of clonal selection of the invention includes at least one of the following steps. First, cell clones capable of growing in commercial serum-free media as suspension cultures are isolated from monolayer cultures of parent Sf-9 cells dependent on serum-containing media by sequential weaning of parent cells from serum-containing media. According to one embodiment depicted in FIG. 2, Sf-9 parent cells are prepared at step 201 for sequential serum-weaning. In this embodiment, monolayer and suspension cultures of Sf-9 cells are grown at about 26–28° C. in a dry environment. Shaker suspension cultures are agitated at about 100–150 rpm in a standard orbital or platform shaker incubator and stir flask suspension cultures are stirred at about 25–75 rpm on a standard laboratory magnetic stirrer.

In step 202, cell aliquots are dispensed from a cell suspension (one cell per aliquot) of the parental cell line in serum-containing media into wells of 96-well dishes at a ratio of one aliquot per well. Following cell attachment, cell acclimation to wells, and exclusion of wells with no cells and wells with more than one cell, in step 202 the media is changed from serum-containing media (100%) to a media mixture comprised of 75% serum-containing media and 25% serum-free media. In step 203, cells are cultured in "75/25" media mixture for approximately one to two weeks. Wells that initially contain only one cell per well and demonstrate cell growth and replication (i.e., four to five cells) after step 203 are subjected in step 204 to another media change to a mixture comprising 50% serum-containing media and 50% serum-free media. In step 205, cells in the "50/50" media mixture of step 204 are allowed to grow for approximately another one to two weeks. The media mixture is changed again in step 206, to a mixture comprising 25% serum-containing media and 75% serum-free media. In step 207, cells are allowed to grow and replicate in the new "25/75" media mixture of step 206. After another two to four weeks, in step 208 the media is changed in wells containing growing cells to a final media comprising serum-free media (100%).

During each step of the weaning process depicted in FIG. 2, a majority of the cells, for example about 95% of the cells or more, do not survive the reduction in serum. While not wanting to be bound by this theory, it is believed that this high level of cell death creates a selective pressure to permit development of a new cell phenotype. In step 209, cells from wells that demonstrate continuous cell growth and replication are harvested by vigorous aspiration with serum-free media. In step 210, the harvested cells are seeded into larger culture flasks (i.e., 75 or 150 cm$^2$ T-flasks), and, in step 211, the suspension cultures are grown. When greater than $4 \times 10^6$ cells with a viability >95% is obtained, cells are harvested in step 211 and seeded into shaker or stir flasks as suspension cultures with a starting cell density, for example, about $0.2$–$0.5 \times 10^6$ cells/ml and a minimal ratio, for example, about 2.5 for total vessel capacity to total volume of culture media. In step 212, cell clones that grow exponentially to a saturation cell density of greater than $6 \times 10^6$ cells/ml in serum-free media are selected, expanded, and frozen.

Finally, one cell clone is selected, passaged for at least 10, preferably at least 20, and more preferably more than 30 times as a suspension culture in serum-free media at a split ratio of at least 1:10, and established as a cell line. This serum-independent cell line is used to establish a master cell bank and subsequent working cell banks.

1.2. Sf-9S Cells

According to another aspect of the invention described herein, there are provided host cells that express one or more recombinant gene products with an enhanced yield. Insect host cells include, for example, Lepidopteran insect cells, and particularly preferred are *Spodoptera frugiperda, Bombyx mori, Heliothis virescens, Heliothis zea, Mamestra brassicas, Estigmene acrea* or Trichoplusia insect cells. Non-limiting examples of insect cell lines include, for example, Sf21, Sf9, High Five (BT1-TN-5B1–4), BT1-Ea88, Tn-368, mb0507, Tn mg-1, and Tn Ap2, among others.

In addition to the serum-weaning process described above, the Sf-9S cells of the present invention have undergone a recombinant peptide secretion selection process. An example of the process of the recombinant peptide secretion selection, according to the invention, is demonstrated in FIG. 3. The Sf-9S cells express extracellularly a foreign recombinant protein with an enhanced yield.

According to one embodiment of the invention, the cells are infected with a recombinant Baculovirus vector to express recombinant proteins or polypeptides of medical, pharmaceutical, or veterinary importance. Baculoviruses including *Autographa californica* multinucleocapsid nuclear polyhedrovirus (AcMNPV) are propagated in cell lines derived from larval tissues of insects of the Lepidopteran insect family. General methods for handling and preparing baculovirus vectors and baculovirus DNA, as well as insect cell culture procedures, are outlined for example in O'Reilly et al., 1994; Vaughn, J. 1999, supra; Frieson et al. 1986. In: *The Molecular Biology of Baculoviruses*, Doerfier et al., Eds. Springer-Verlag, Berlin, pages 31–49; Kool et al, 1993. *Arch. Virol.* 130: 1–16, incorporated herein by reference in their entirety.

In one embodiment, polynucleotide molecules, including chimeric and heterologous polynucleotides, which encode a foreign peptide of interest, are inserted into the baculovirus genome operably coupled to or under the control of the polyhedrin or other Baculovirus promoters. The recombinant baculovirus vector is then used to infect a host cell. The foreign peptide or protein is expressed upon culture of the cells infected with the recombinant virus.

In another embodiment, the invention provides a method for producing a selected foreign protein in an insect cell. The method comprises preparing infected insect cells that express at least a first recombinant viral protein, and infecting the transformed cell with a baculovirus comprising an expression vector that encodes a second recombinant viral protein. The first, or the second viral proteins, or both are, for example, viral capsid proteins including heterologous peptides and chimeric peptides. The transformed cells produced according to the method disclosed herein produce substantially high yields of recombinant baculoviruses expressing the desired recombinant peptides.

The insect cells of the invention have passed through a recombinant peptide secretion selection. As described herein, the process of recombinant peptide secretion selection includes one or more of the following steps. Cells from a serum-weaned clone are infected with a first baculovirus expressing a first recombinant protein. Cells capable of secreting high levels of the first recombinant protein are selected further for infection with a second baculovirus expressing a second recombinant protein. Cells from a clone that secretes high levels of both recombinant proteins independently are passaged further to establish a Sf-9S cell line of the present invention.

According to a preferred embodiment, the first recombinant protein or the second recombinant protein, or both, is a viral capsid protein that self-assembles into virus-like particles. In a more preferred embodiment, the virus-like particles are derived from viral capsid proteins of an enveloped virus, or a non-enveloped virus, including, but not limited to, an influenza virus, a hepatitis C virus, a retrovirus such as a human immunodeficiency virus, a rotavirus, a calicivirus, a hepatitis E virus, a papillomavirus, or a combination thereof In a most preferred embodiment of the invention, the virus-like particles are derived from human papillomavirus.

According to a preferred embodiment of the invention, the Sf-9S cells support intracellular, and preferably extracellular, expression of recombinant proteins and macromolecules. More preferably, infected SF-9S cells extracellularly express viral capsid proteins that self assemble into VLPs. Virus-like particles typically self assemble in the cell and remain intracellular; therefore isolation of these particles requires processes of cell disruption and protein solubilization with the accompanying risks of VLP disruption, proteolysis and contamination of the end product. Accordingly, the infected cells of the invention that afford self-assembly of viral capsid antigens into VLPs and facilitate secretion of VLPs extracellularly are highly desirable.

Figure 3:
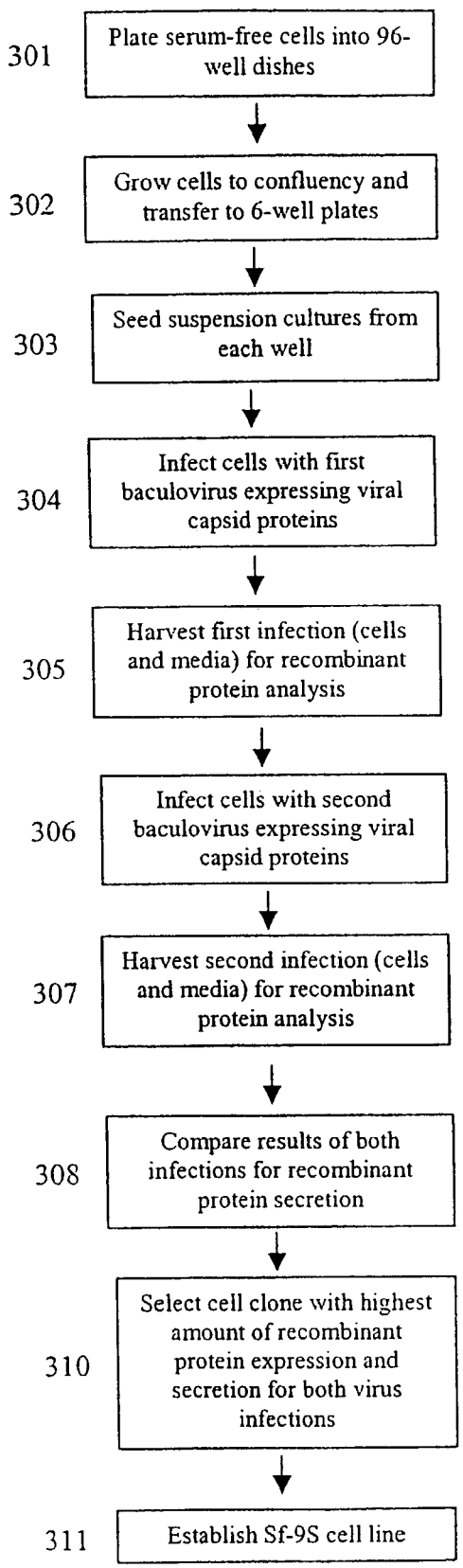
FIG. 3 shows a schematic flowchart of the steps in the protein secretion selection process of an insect cell line capable of growing in serum-free media as suspension cell cultures and of enhanced expression of extracellular recombinant proteins and virus-like particles.

An example of a process for recombinant peptide secretion selection as depicted in FIG. 3 is described below. FIG. 3 demonstrates that additional rounds of clonal selection are used to obtain cells capable of enhanced secretion of recombinant proteins. In step 301, cell aliquots from a cell suspension (one cell per aliquot) of the parent serum-free cell clone (i.e., a cell line from one of the serum-free cell clones selected in step 213 of FIG. 2) are replica-plated into each well of 96-well plates at a ratio of one cell per well. In step 302, wells containing a single cell from the original seeding are identified and grown to confluency. Upon confluency, cells from wells identified as single cell wells are subcultured into replica plates in step 303. Cells in replica plates are grown at step 304 to confluency and infected with a first recombinant baculovirus expressing first virus capsid proteins that are capable of self-assembly into virus-like particles.

During baculovirus infection, in step 305 the infected cells and extracellular media are harvested by centrifugation to isolate infected cells and extracellular media, heat-denatured under reduced conditions (>75° C. for 5 minutes in 1% sodium dodecyl sulfate (SDS) and 10 mM β-mercaptoethanol), and analyzed by SDS-PAGE and Western blot analyses with antisera to viral capsid proteins. In step 306, cells in replica plates that contain cell clones exhibiting extracellular VLPs at levels higher than control Sf-9 cells are infected with a second baculovirus expressing the second viral capsid proteins that self-assemble into virus-like particles. The infected cells and extracellular media from the second selection round are isolated in step 307 by centrifugation and analyzed by SDS-PAGE and Western blot analyses. The first and second viral capsid proteins are the same or different proteins and include, for example, rotavirus VP2, VP6, and HPV-16 L1, HPV-L2 proteins, among others.

The test results from the first and second rounds of selection (i.e. virus infections producing VLPs) are examined in step 308. The cell clone exhibiting the highest levels of extracellular VLPs from both virus infections is chosen in step 310. From the replica plate, cells of the selected cell clone exhibiting highest extracellular VLP levels are passaged repeatedly in suspension culture with serum-free insect cell media to establish a cell line. The cell line supports high levels of extracellular VLP production upon infection with recombinant baculoviruses expressing viral capsid proteins that self-assemble into virus-like particles. Thus, in one embodiment, the clone selected in step 310 is processed again according to steps 304–309 with recombinant baculovirus expressing HPV-16 L1 capsid proteins. The cell clone that produces the highest levels of extracellular VLPs for both sets of viral capsid proteins is chosen in step 311 to establish a cell line capable of producing extracellular VLPs.

Master cell banks of Sf-9S cells are established, for example, from a single cell passage of the new cell line grown in suspension culture of serum-free medium and stored at −70° C. in liquid nitrogen in a cryopreservation freezing media containing fresh serum-free media, conditioned serum-free media, and dimethyl sulfoxide. Working cell banks are developed, for example, from single cryovials of the master cell bank, subjected to safety and biological testing for qualification as a host cell substrate for manufacturing of recombinant protein products, and stored at −70° C. in liquid nitrogen in cryovials in cryopreservation freezing media as described above.

The Sf-9S cell line of the present invention demonstrate one or more of the following properties: (1) they replicate in serum-free media; (2) they are genetically distinct from parent Sf-9 parent cell line; (3) they grow as single cells in suspension cultures; (4) they demonstrate cell division rate of approximately 18–24 hours; (5) they demonstrate high cell viability (more than 95%) upon continuous cell culture for more than one year; (6) they constitute a cell substrate for *Autographa californica* baculoviruses to produce high-titered virus stocks (more than $10^7$ plaque forming units (pfu)/ml); (7) they are suitable for recombinant protein expression and production from baculovirus vectors; (8) they are suitable host cell substrates for agarose plaque assays to titer baculovirus stocks; (9) they are compliant with recognized identity and safety guidelines; (10) they are suitable cell substrates for large-scale manufacturing of human and animal biological products including vaccines, therapeutics, and diagnostic reagents; (11) they are suitable cell substrates for transfection of genes in recombinant baculovirus transfer vectors and/or bacmids to produce recombinant baculoviruses, and (12) they produce high levels of extracellular VLPs from baculoviruses expressing viral capsid proteins that self-assemble into VLPs of non-enveloped viruses such as rotaviruses, caliciviruses, hepatitis E virus, and human papillomaviruses and of enveloped viruses such as influenza virus, hepatitis C virus, and human immunodeficiency virus.

Figure 4:
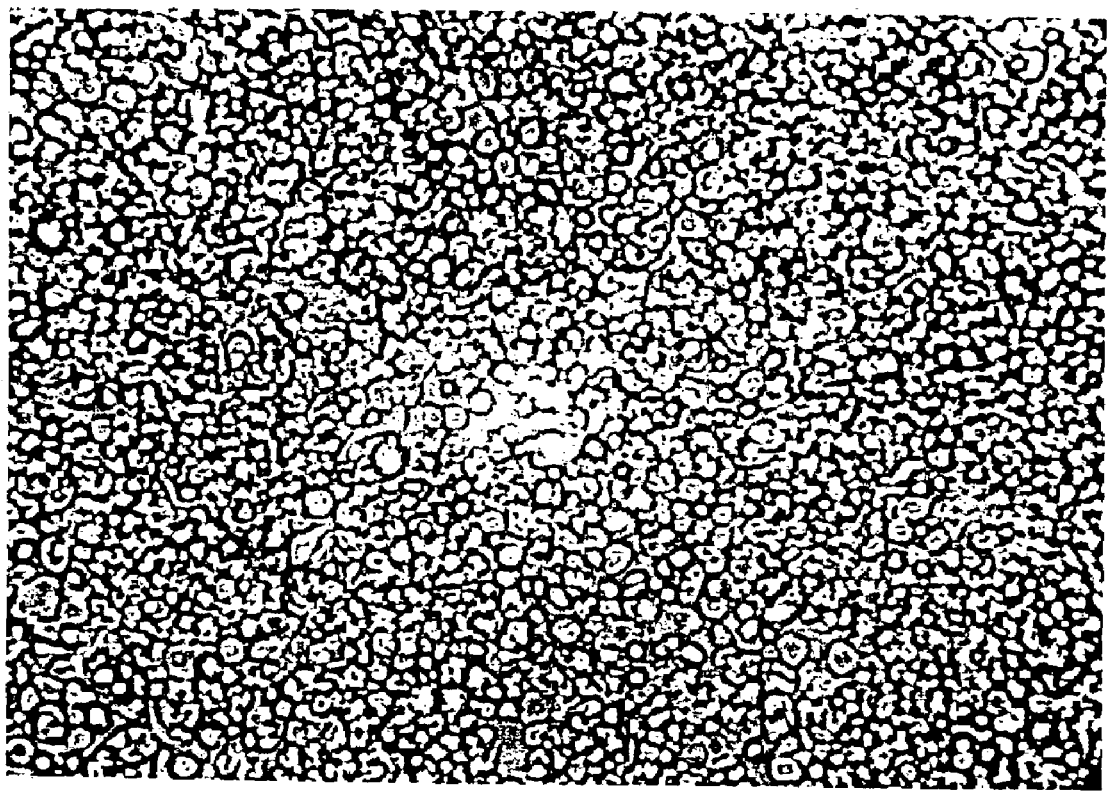
FIG. 4 shows a photomicrograph of a confluent monolayer of Sf-9S insect cells grown in serum-free insect cell media (Sf-900 II SFM, GIBCO) visualized by inverted phase-contrast microscopy at 400× magnification using Kodachrome 100 color film (Kodak).
Figure 5:
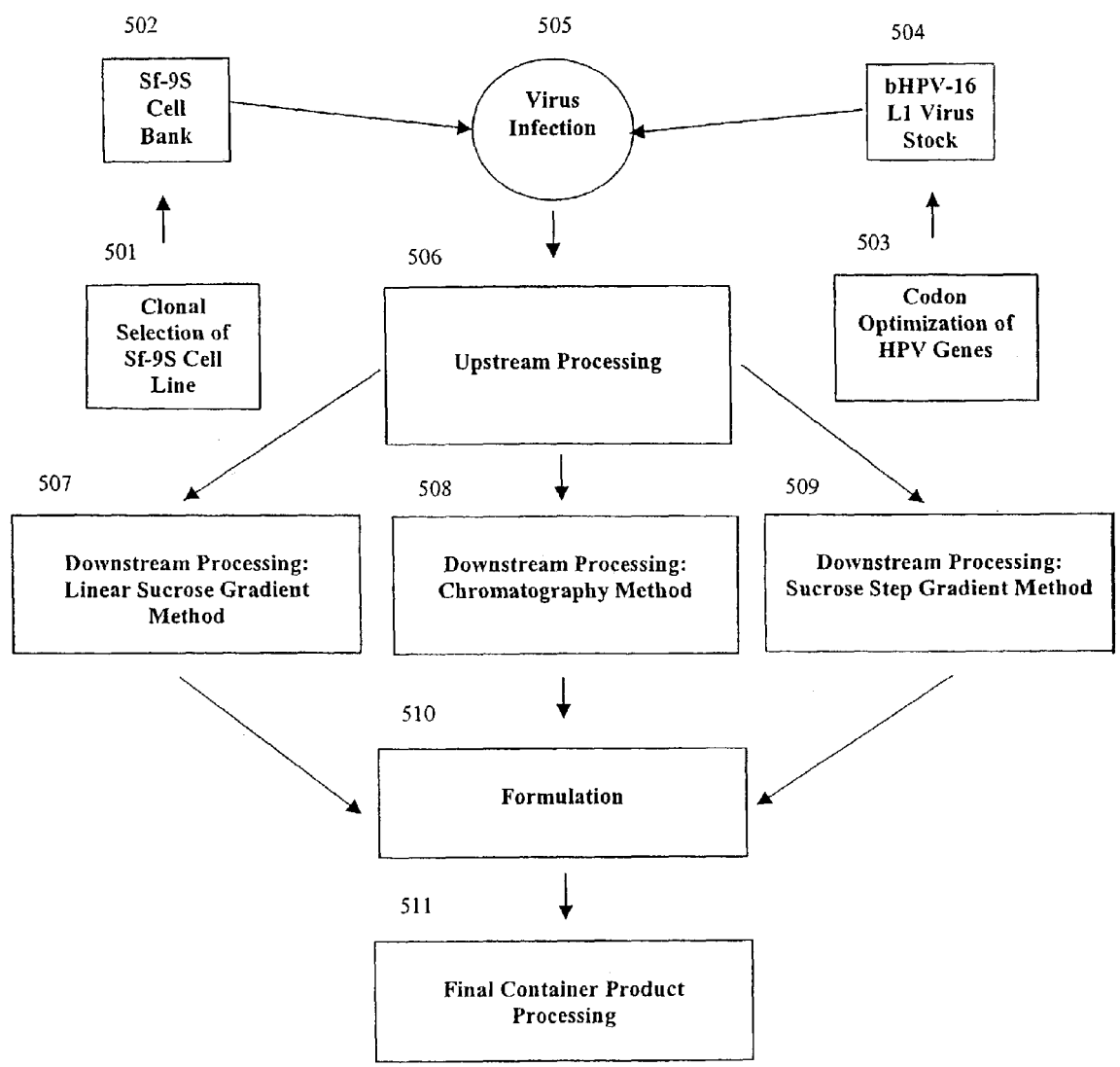
FIG. 5 shows a schematic flowchart of the basic steps in the production or manufacturing of purified HPV VLP products according to the present invention.
Figure 6:
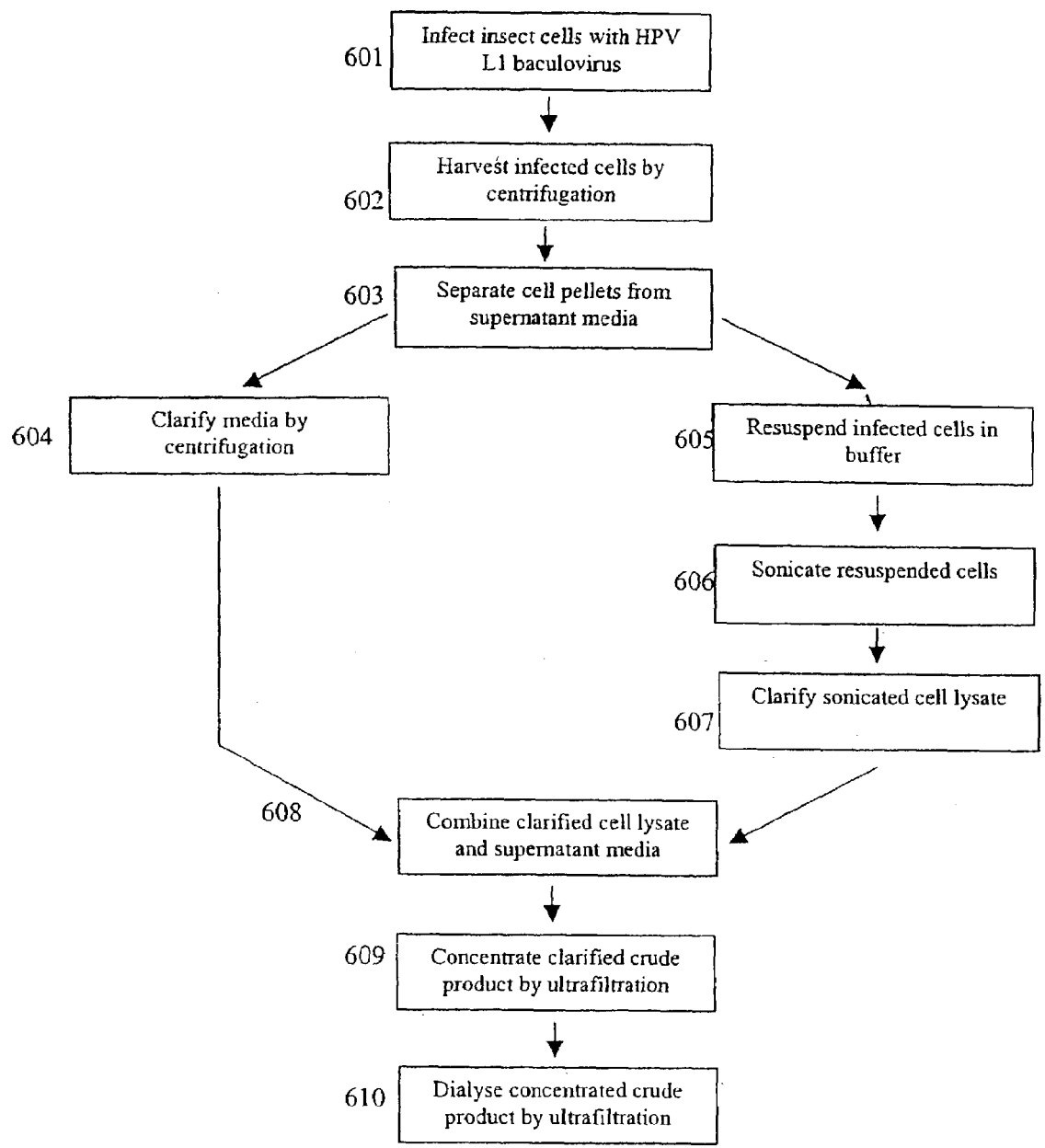
FIG. 6 shows a schematic flowchart of an upstream processing of baculovirus-infected insect cell suspensions for production of recombinant HPV L1 VLPs according to the present invention.
Figure 7:
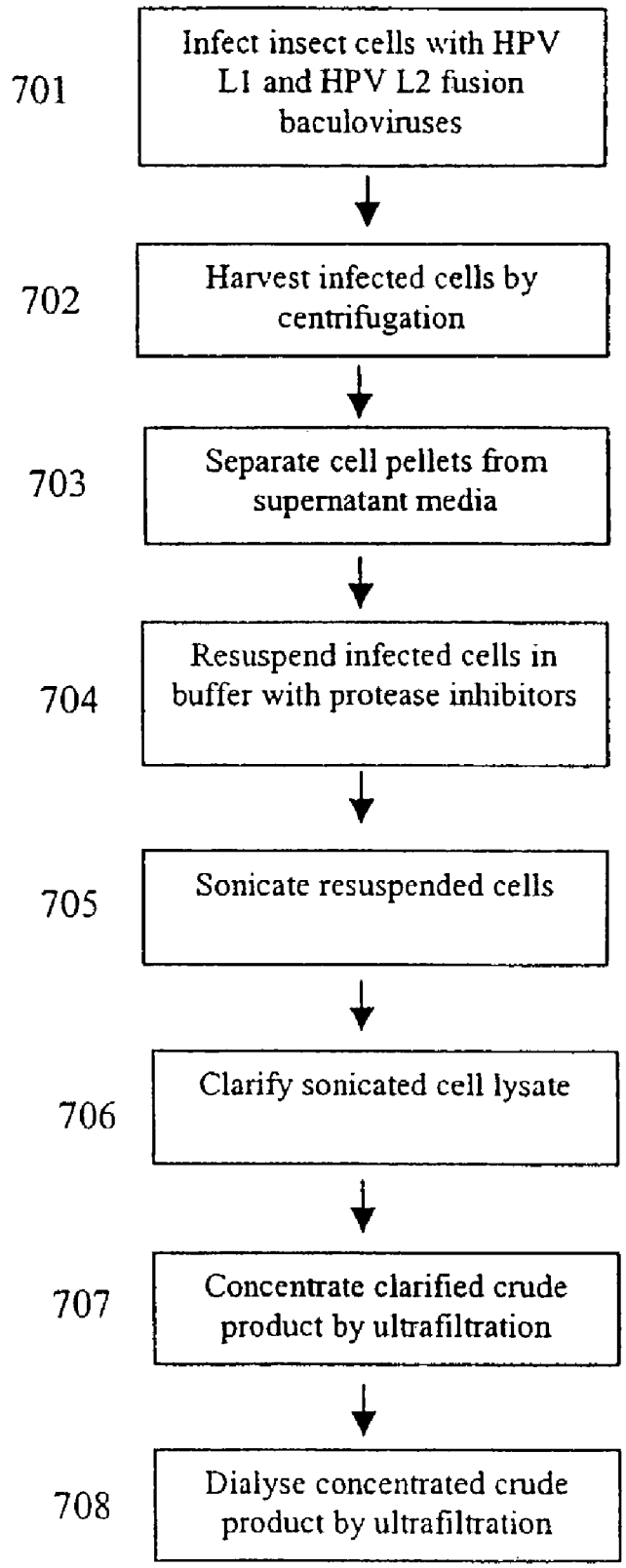
FIG. 7 shows a schematic flowchart of one set of steps in upstream processing of baculovirus-infected insect cell suspensions for production of recombinant HPV chimeric VLPs according to the present invention.
Figure 8A:
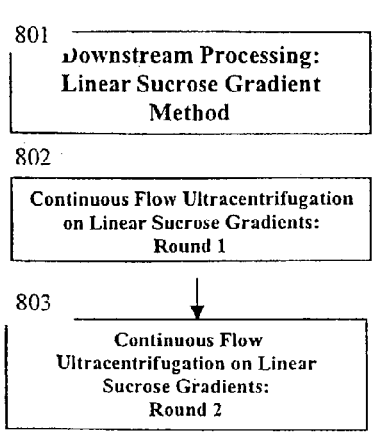
FIG. 8A shows a schematic flowchart of one set of steps in downstream processing for purification of recombinant HPV VLPs by continuous flow ultracentrifugation using linear sucrose gradients according to the present invention.
Figure 8B:
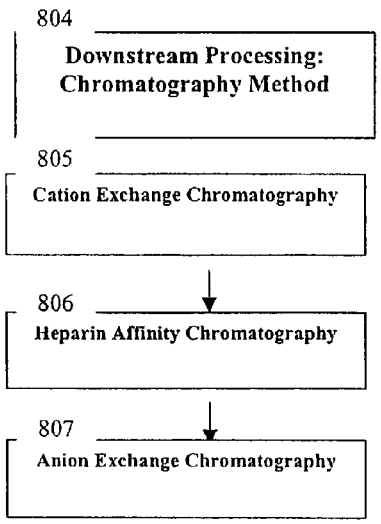
FIG. 8B shows a schematic flowchart of another set of steps in downstream processing for purification of recombinant HPV VLPs by column chromatograph using ion exchange and affinity binding matrices according to the present invention.
Figure 8C:
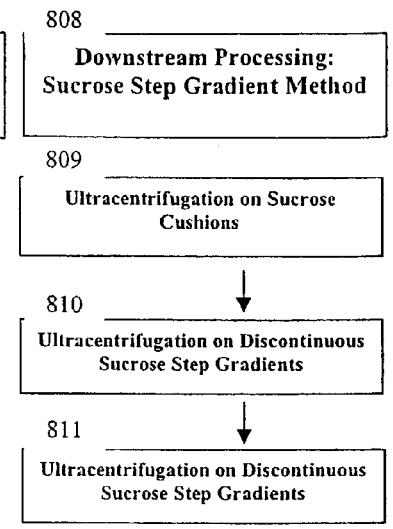
FIG. 8C shows a schematic flowchart of a different set of steps in downstream processing for purification of recombinant HPV VLPs by ultracentrifugation using discontinuous sucrose step gradients according to the present invention.
Figure 9:
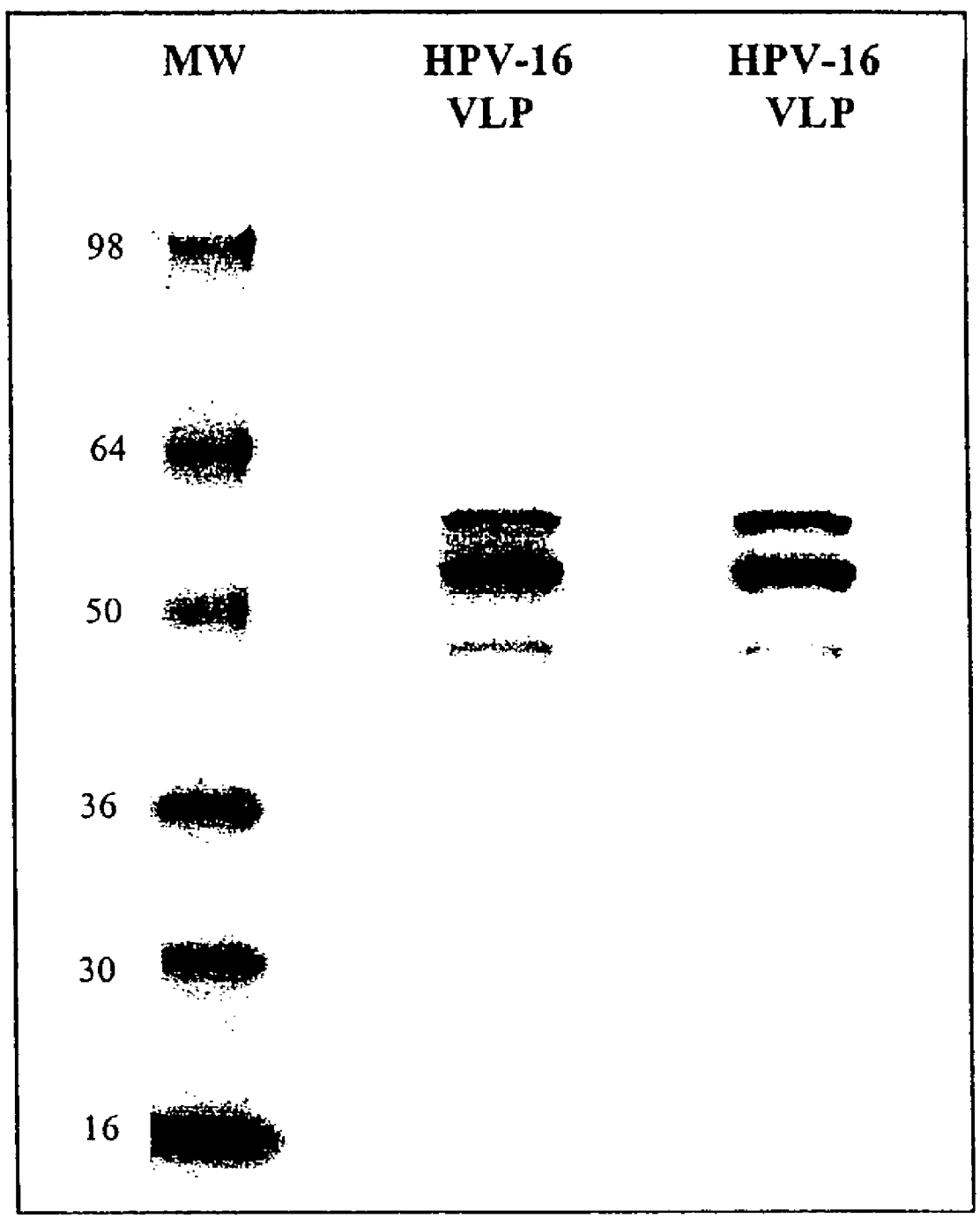
FIG. 9 shows a stained protein gel of the products of the invention (i.e., baculovirus-derived recombinant HPV-16 L1 VLPs purified according to the methods of the present invention.
Figure 10:
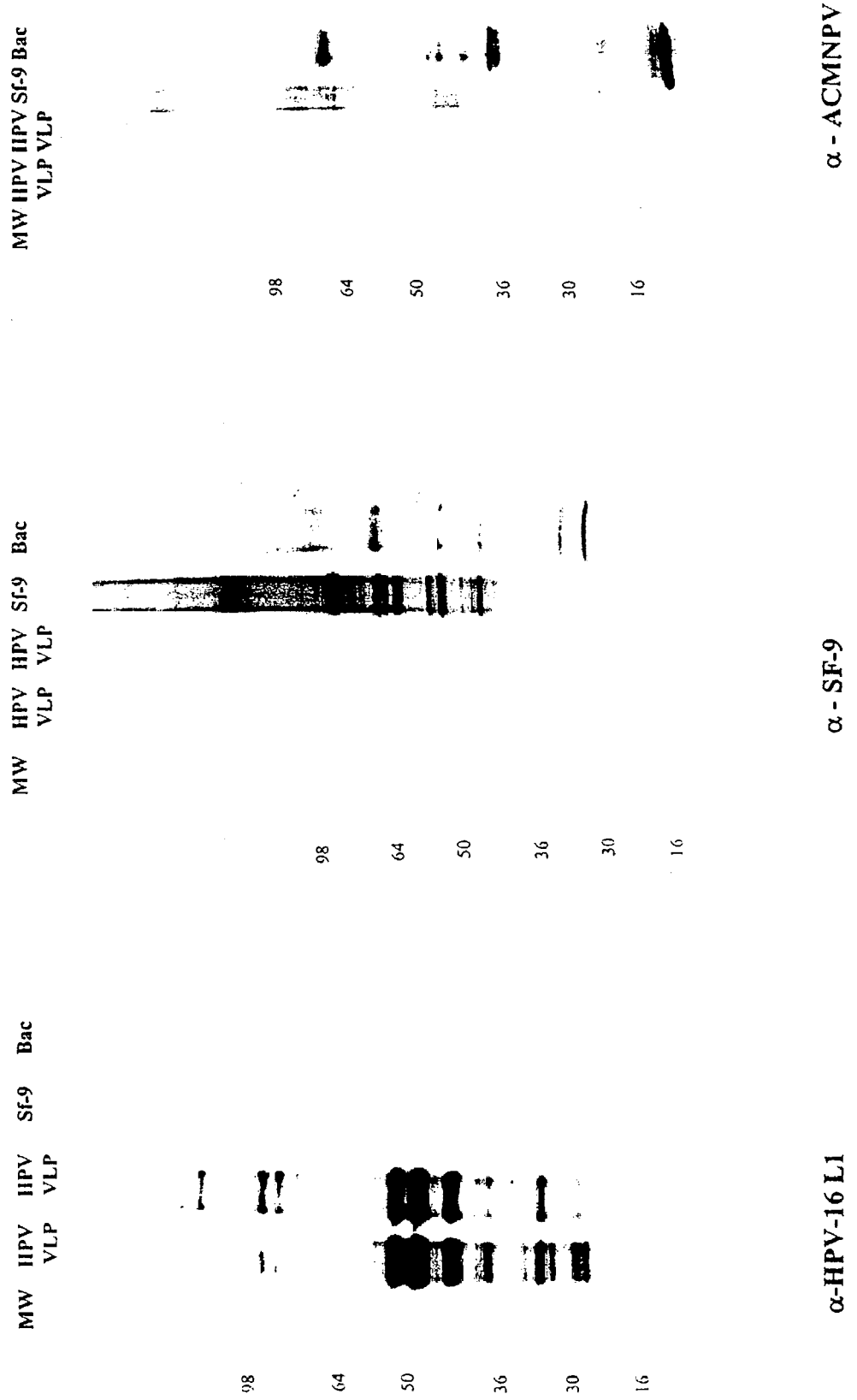
FIG. 10A shows proteins detected chromogenically on membranes by Western blot analysis of recombinant HPV-16 L1 VLPs purified according to the methods of the present invention and bound to polyclonal antisera to HPV-16 L1 protein (1:10,000).
FIG. 10B shows proteins detected chromogenically on membranes by Western blot analysis of recombinant HPV-16 L1 VLPs purified according to the methods of the present invention and bound to polyclonal antisera to Sf-9S insect cell proteins (1:500).
Figure 11:
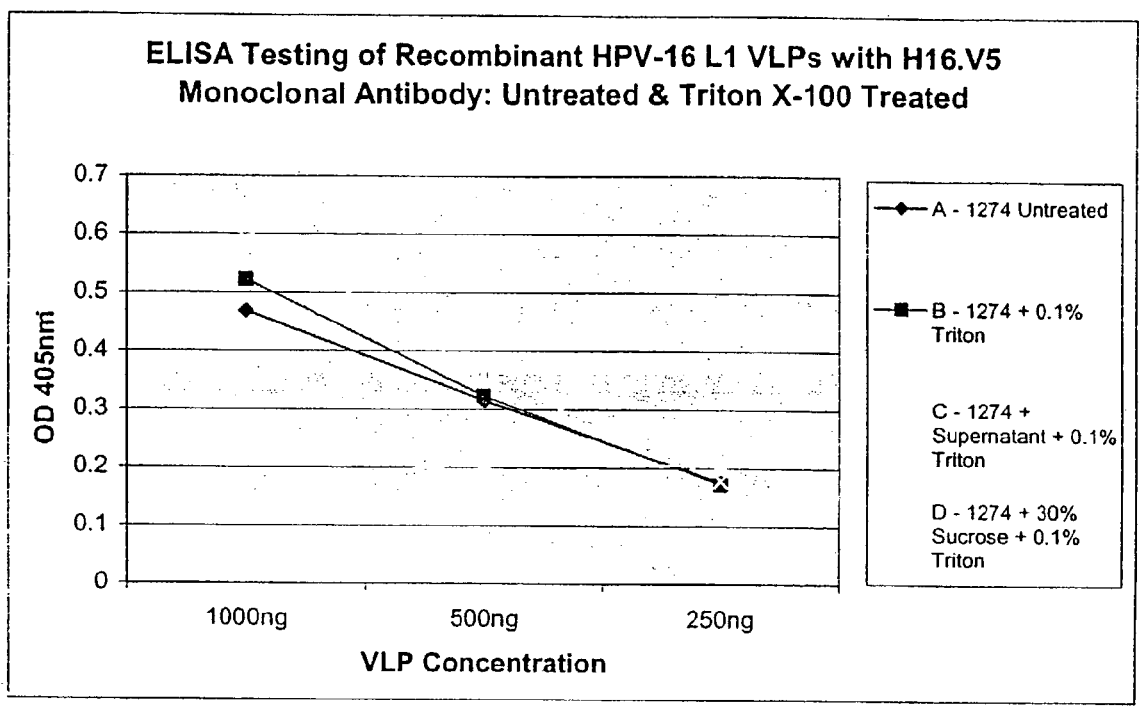
FIG. 11 shows a graph of the binding results of H16.V5 murine monoclonal antibody to conformational epitopes on untreated and Triton X-100-treated recombinant HPV-16 L1 VLPs purified and treated according to the methods of the present invention as measured by enzyme linked immunoadsorbent assay (ELISA) analysis.
Figure 12:
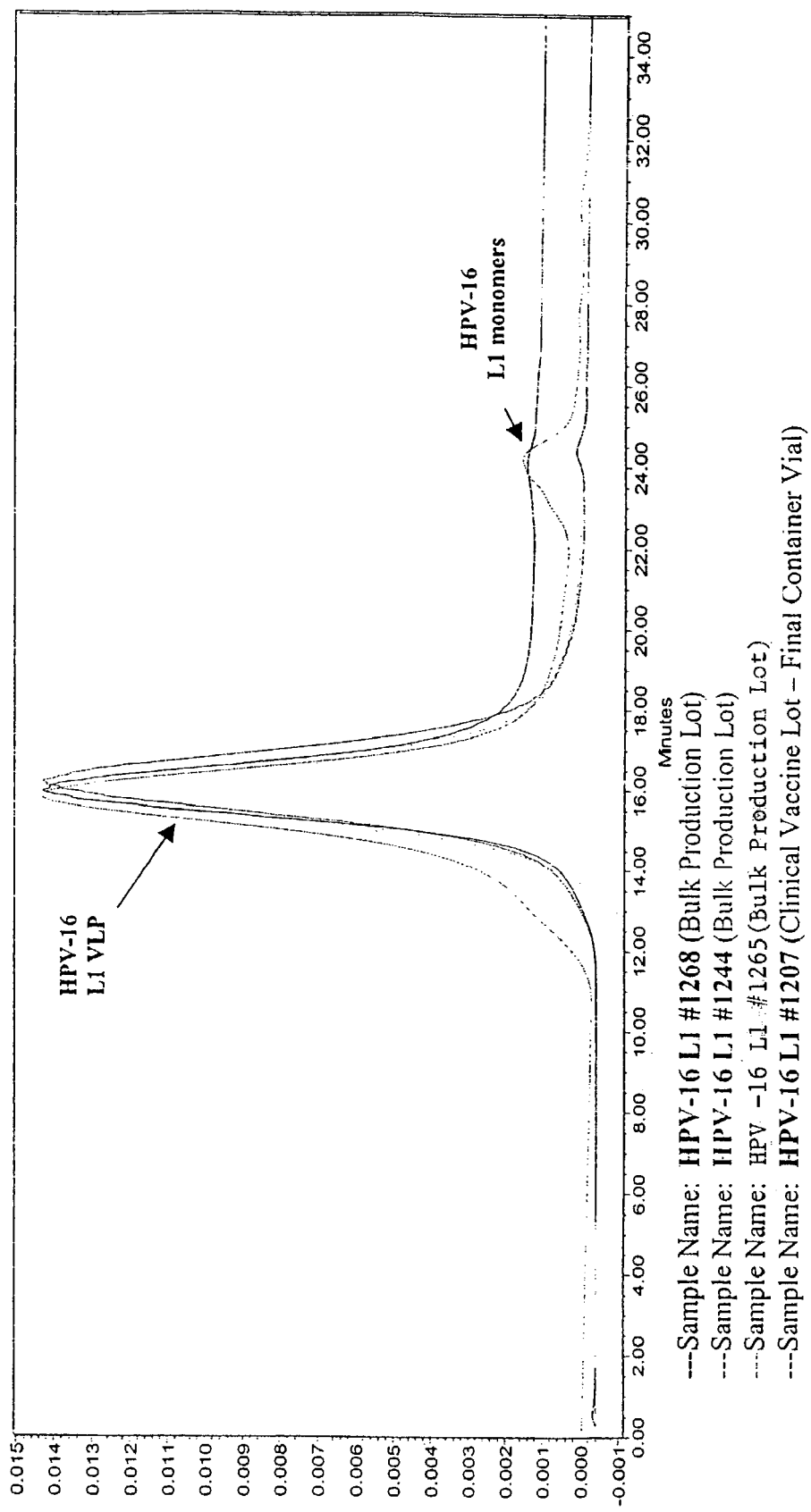
FIG. 12 shows a chromatogram of a product of the invention, recombinant HPV-16 L1 VLPs purified according to the methods of the present invention, analyzed by analytical size exclusion chromatography.
Figure 13:
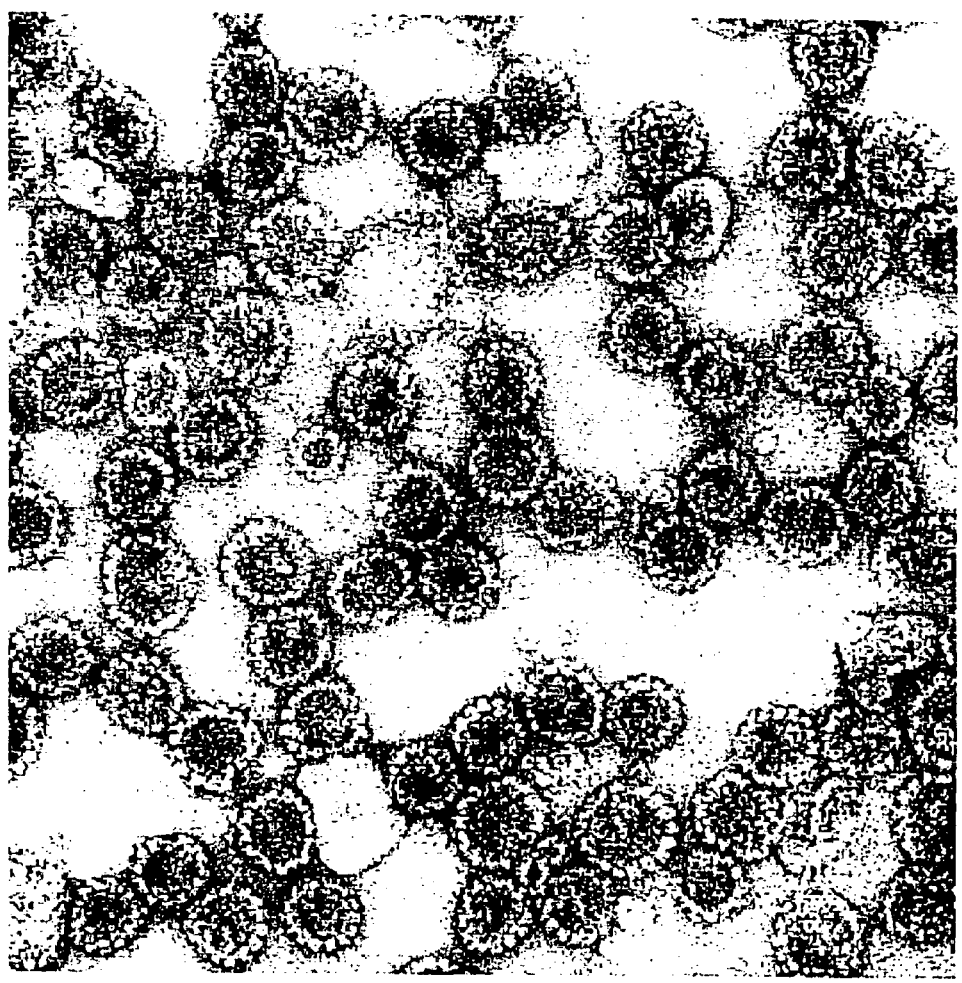
FIG. 13 shows an electron micrograph of baculovirus-derived recombinant HPV-16 L1 VLPs purified according to the methods of the present invention, stained negatively with uranyl acetate, and magnified 36,000×. The bar scale is 50 nm.

In FIG. 4, a confluent monolayer of Sf-9S cells grown in serum-free insect cell media is shown at 400× magnification using a phase-contrast microscope. The cuboidal and fibroblastic cell morphologies of the cell line are displayed. The cell morphology of Sf-9S cells changes from fibroblastic to cuboidal, as the monolayer becomes confluent.

Safety testing of the Sf-9S cell line produced according to the present invention and deposited at the ATCC may be performed in accordance with United States federal regulatory guidelines and include microbial sterility, mycoplasma and spiroplasma growth, endotoxins, adventitious agents (in vitro and in vivo assays), and electron microscopic examination for type C endogenous retrovirus particles. The cell identity of the Sf-9S cell line was shown by karyology and isotype enzyme analyses, to be *S. frugiperda* insect species with the typical polyploid chromosomal pattern distinct from mammalian cells.

2. Virus-Like Particles (VLPs)

The present invention provides methods of producing and purifying intact recombinant virus-like particles that retain their conformational epitopes which elicit antigen neutralizing antibodies and provide protective immunity.

Encompassed within the scope of the invention are VLPs that are made with capsid protein of non-enveloped and enveloped viruses, including rotaviruses, caliciviruses, hepatitis E virus, and human papillomaviruses, influenza virus, hepatitis C virus, and human immunodeficiency virus. Preferably, the VLPs are made with Papillomavirus L1 capsid protein.

Also encompassed within the scope of the invention are VLPs derived from different species and genotypes of the papillomaviruses. Papillomaviruses of the invention are derived, for example, from human, simian, bovine, or other origins. Preferably, the papillomavirus of the invention is a human papillomavirus (HPV). More than 60 different human papillomavirus (HPV) genotypes have been isolated. Human papillomavirus genotypes include, but are not limited to, HPV-16, HPV-18, and HPV-45 for high-risk cervical cancers; HPV-31, HPV-33, HPV-35, HPV-51, and HPV-52 for intermediate-risk cervical cancers; and HPV-6, HPV-11, HPV-42, HPV-43, and HPV-44 for low-risk cervical cancer and anogenital lesions (Bosch et al., 1995; Walboomers et al., 1999). HPV genotypes are also disclosed in PCT publication No. WO 92/16636 (Boursnell et al., 1992), incorporated herein by reference in its entirety. HPV-16 is a preferred genotype of the invention.

2.1. Codon Optimized VLPs

According to one embodiment of the invention, there are provided codon optimized polynucleotides that encode one or more viral proteins. The codon optimization of the invention is based on the following criteria: (1) abundance of aminoacyl-tRNAs for a particular codon in Lepidopteran species of insect cells for a given amino acid as described by Levin and Whittome (2000), (2) maintenance of GC-AT ratio in gene sequences at approximately 1:1, (3) minimal introduction of palindromic or stem-loop DNA structures, and (4) minimal introduction of transcription and post-transcription repressor element sequences. The gene sequences are synthesized in vitro as overlapping oligonucleotides, cloned and expressed in host cells. Cloning and expression of the codon modified viral genes were achieved following the methods known in the art and exemplified at Examples 3 and 4.

In a preferred embodiment of the invention, polynucleotides encoding a viral gene, for example HPV L1 gene, are optimized for expression in a baculovirus-infected insect cell, comprising the steps of: (a) replacing nucleotide sequences of codons in the gene that are underutilized in insect cells of Lepidopteran species with sequences of preferred codons in insect cells; and (b) for each amino acid encoded by this modified nucleotide sequence, if a plurality of codons for the same amino acid is preferred in insect cells, then the nucleotide sequence of the modified gene is changed further by selecting a codon from preferred codons for a amino acid so that (i) the ratio of GC nucleotides to AT nucleotides in the sequence trends toward 1:1; (ii) the number of palindromic and stem-loop structures is minimized unless indicated otherwise for functional activity; and (iii) the number of transcription and/or post-transcription repressor elements in the sequence is minimized. This method was used to develop the genes encoding HPV-16 L1 codon modified polynucleotides shown in SEQ ID NO. 1.

The method of codon optimization of the invention, as described herein, is used to optimize the expression of a variety of enveloped and non-enveloped viral genes expressed in insect cells.

2.2 Chimeric VLPs

Chimeric VLPs refer to viral capsid proteins that encapsulate other viral proteins or heterologous gene products. A preferred chimeric VLP according to the invention is a papillomavirus L1 capsid protein, or peptide fragment thereof, which encapsulate other papillomavirus gene products or heterologous gene products during self-assembly into virus-like particles. For example, gene products containing the HPV L2, E2, E6, and/or E7 gene products become encapsulated into the HPV L1 VLPs and are considered herein as chimeric VLPs.

Papillomavirus genes (including human papillomavirus genes) are used to develop nucleotide sequences for HPV L2 (including wildtype L2), L2/E7, L2/E7/E2, and L2/E6 gene sequences optimized for expression in insect cells. These gene sequences encode L2 proteins L2/E7, L2/E7/E2 and L2/E6 proteins, among others.

Codon optimization of gene sequences comprising chimeric VLPs is achieved in the same way as for L1 VLPs. The codon optimized L2 and L2 fusion genes, as disclosed and described herein, include, HPV L2 (SEQ ID NO. 2), HIV L2/E7 (SEQ ID NO. 3), HPV L2/E7/E2 (SEQ ID NO. 4), and HPV L2/E6 (SEQ ID NO. 5), respectively.

The cloning and expression of the L2 and L2 fusion genes were achieved following the methods known in the art. One example of such methods is exemplified at Example 4 herein.

2.4. Substantially Homologous Polynucleotides

The codon optimized polynucleotides of the invention include polynucleotide sequences that have at least 50%, 65%, 70%, 75%, 80%, 85%, 90%, 95%, 98%, 99% or more nucleotide sequence identity to the codon optimized polynucleotide, or contain a transcriptionally active fragment. To determine the percent identity of two nucleic acid sequences, the sequences are aligned for optimal comparison purposes (i.e., gaps can be introduced in the sequence of a first nucleic acid sequence for optimal alignment with a second nucleic acid sequence). The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences (i.e., % identity=# of identical overlapping positions/total # of positions×100). In one embodiment, the two sequences are the same length.

The determination of percent identity between two sequences also can be accomplished using a mathematical algorithm. A preferred, non-limiting example of a mathematical algorithm utilized for the comparison of two sequences is the algorithm of Karlin and Altschul (1990) *Proc. Natl. Acad. Sci.* USA 87:2264–2268, modified as in Karlin and Altschul (1993) *Proc. Natl. Acad. Sci.* USA 90:5873–5877. Such an algorithm is incorporated into the NBLAST program of Altschul, et al. (1990) *J. Mol. Biol.* 215:403–410. BLAST nucleotide searches can be performed with the NBLAST program, score=100, wordlength=12 to obtain nucleotide sequences homologous to a nucleic acid molecules of the invention. To obtain gapped alignments for comparison purposes, Gapped BLAST can be utilized as described in Altschul et al. (1997) *Nucleic Acids Res.* 25:3389–3402.

Alternatively, PSI-Blast can be used to perform an iterated search which detects distant relationships between molecules (Id.). When utilizing BLAST, Gapped BLAST and PSI-Blast programs, the default parameters of the NBLAST program can be used (see, for example, www.ncbi.nlm.nih.gov). Another preferred, non-limiting example of a mathematical algorithm utilized for the comparison of sequences is the algorithm of Myers and Miller, (1988) CABIOS 4: 11–17. Such an algorithm is incorporated into the ALIGN program (version 2.0) which is part of the GCG sequence alignment software package. In an alternate embodiment, alignments can be obtained using the NA_MULTIPLE_ALIGNMENT 1.0 program, using a Gap Weight of 5 and a GapLength Weight of 1.

3. Expression Systems

The expression vector of the invention is a baculovirus vector. For baculovirus vectors and baculovirus DNA, as well as insect cell culture procedures, see, for example in O'Reilly et al. 1994, incorporated herein by reference in its entirety. The baculovirus vector construct of the invention preferably contains additional elements, such as an origin of replication, one or more selectable markers allowing amplification in the alternative hosts, such as *E. coli* and insect cells.

In certain embodiments, there are provided baculovirus vectors that contain cis-acting control regions effective for expression in a host operatively linked to the polynucleotide to be expressed. Appropriate trans-acting factors are either supplied by the host, supplied by a complementing vector or supplied by the vector itself upon introduction into the host.

Host cells are genetically transformed to incorporate codon optimized polynucleotides and express polypeptides of the present invention. The recombinant vectors containing a polynucleotide of interest are introduced into the host cell by any of a number of appropriate means, including infection (where the vector is an infectious agent, such as a viral or baculovirus genome), transduction, transfection, transformation, electroporation, microprojectile bombardment, lipofections, or a combination thereof. A preferred method of genetic transformation of the host cells, according to the invention described herein, is infection.

The polynucleotides are introduced alone or with other polynucleotides. Such other polynucleotides are introduced independently, co-introduced or introduced joined to the polynucleotides of the invention. Thus, for instance, a polynucleotides (i.e., L1 gene) is transfected into host cells with another, separate polynucleotide (i.e., L2 or fusion L2 genes) using standard techniques for co-transfection and selection. In another embodiment, the polynucleotides encoding L1 capsid protein and the polynucleotides encoding L2 protein or an L2 fusion protein are present on two mutually compatible baculovirus expression vectors which are each under the control of their own promoter.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims. The contents of all references, patents and published patent applications cited throughout this application are expressly incorporated herein by reference.

EXAMPLES

Example 1

Establishment of Serum-Free SF-9 Insect Cell Line

A new insect cell line designated Sf-9S was derived from the parent *S. frugiperda* Sf-9 cell line [ATCC CRL-1771] by several rounds of selective processes based on serum-independent growth and enhanced expression of secreted recombinant proteins from baculovirus vectors. Specifically, Sf-9 cells were cultivated to passage 38 in Grace's insect media (Life Technologies, Grand Island, N.Y. 14072) supplemented with 10% fetal bovine serum (Life Technologies, Grand Island, N.Y. 14072) as monolayer cultures in T-75 flasks (Corning, Inc., Corning, N.Y.). The master cell bank of Sf-9 cells was stored at passage 38 in serum-containing media at −70° C. and in liquid nitrogen. A working cell bank was established from a single cryovial of the Sf-9 master cell bank and cultivated in serum-containing insect media for an additional five (5) passages.

Initially, cell clones capable of growing in commercial serum-free media as suspension cultures were isolated from monolayer cultures of parent Sf-9 cells dependent on serum-containing media by sequential weaning of parent cells from serum-containing media. This process involved the plating of cell aliquots (200 µl) from a cell suspension (one cell per 200 µl) of the parent cell line in serum-containing media onto 96-well dishes at a ratio of 200 µl per well. Following attachment of cells and inspection of wells for wells with more than one cell, the media was changed from serum-containing media (100%) to a media mixture comprised of 75% serum-containing media and 25% serum-free media. After one to two weeks in culture, the media was changed from wells that initially contained only one cell per well and demonstrated cell growth and replication (i.e. four to five cells).

The second media mixture was comprised of 50% serum-containing media and 50% serum-free media. The cells were allowed to grow for another one to two weeks. The media was changed from wells containing cells that continued to grow and replicate. The third media mixture was comprised of 25% serum-containing media and 75% serum-free media. The cells were allowed to grow and replicate. After another two to four weeks, the media was changed from wells containing cells that continued to grow and replicate. The final media was comprised of serum-free media (100%). During each round of the weaning process, more than 90% of the cells did not survive the reduction in serum. This high level of cell death created a selective pressure to permit development of a new cell phenotype. Cells from wells that demonstrated continuous cell growth and replication were harvested and seeded into larger culture vessels. When a total cell density of >4×10$^6$ cells was obtained, cells were seeded into shaker flasks (50 ml) as 10 ml suspension cultures with a starting cell density of 0.2–0.5×10$^6$ cells/ml. Eight (8) clones that grew exponentially to a saturation cell density of >6×10$^6$ cells/ml in serum-free media was selected, expanded, and frozen. One of the clones was established as a serum-free independent cell line.

Example 2

Establishment of SF-9S Cell Line

In a second selection process, one of the serum-free cell clones developed in Example 1 was chosen to select cell clones that may produce enhanced levels of recombinant extracellular proteins and VLPs from several viruses including rotaviruses and human papillomaviruses by successive rounds of clonal selection of cells infected with recombinant baculoviruses and expressing extracellular self-assembled VLPs.

This process involved the plating of cell aliquots (200 µl) from a cell suspension (one cell per 200 µl) of the parent cell clone (#23) in serum-free media onto 96-well dishes at a ratio of 200 µl per well. From wells containing a single cell in the original seeding, cells were grown to confluency and subcultured into six replica-plates (96-well). The first round of selection was performed when a total cell density of 2–4×10$^3$ cells/well was obtained, the cells were infected with recombinant baculoviruses encoding human rotavirus virus VP2 and VP6 capsid genes. After three days of baculovirus infection, the infected cells and extracellular media were harvested by centrifugation. Infected cells were solubilized by adding 250 µl of 1% sodium dodecyl sulfate (SDS) and 10 mM β-mercaptoethanol (β-ME). SDS and β-ME were added to extracellular supernatants to final concentrations of 1% and 10 mM, respectively. Aliquots (10 µl) of solubilized cell lysates and extracellular media were heat-denatured (99° C. for 10 min.) under reduced conditions and analyzed by SDS-PAGE and Western blotting using antisera to rotaviruses.

After review of the test results from the first virus infection, twenty four (24) cell clones demonstrating the highest levels of extracellular recombinant rotavirus VLPs were identified, seeded into 96-well plates, grown to confluency, and infected with a second recombinant baculovirus encoding HPV-16 L1 capsid protein. At three days post-infection, infected cells and extracellular supernatants were produced by centrifugation of infected cell suspensions from the plate.

Infected cells and extracellular supernatants were analyzed by SDS-PAGE and Western blot analyses using polyclonal anti-HPV-16 L1 sera. The test results of both viral infections were reviewed and compared. One cell clone (#12) that produced the high levels of extracellular VLPs from rotavirus and HPV capsid proteins was chosen to establish a cell line capable of producing extracellular VLPs. To establish a cell line from the selected cells, cells from an uninfected replica plate were amplified at 28° C. and 150 rpm in a platform shaker incubator into a suspension culture using Sf-900 II serum free media (GIBCO). The amplified cell culture was diluted to a seeding cell density of 0.25×10$^6$ cells/ml, grown in 100 ml of Sf-900 II SFM within a 500 ml shaker flask, and subcultured at a split ratio of 1:20 for forty three passages. After continuous passaging, the cell line was established and was passaged three more times to establish a master cell bank.

Example 3

Cloning Codon-Optimized HPV-16 L1 Genes and Establishment of Recombinant Baculovirus Stocks A HPV-16 L1 prototype (GenBank Accession No. K02718) and modified in U.S. Pat. No. 5,985,610, was optimized for codon usage in insect cells of the Lepidopteran family. The HPV-16 L1 gene was optimized (FIG. 1A) in this embodiment of the present invention for codon usage based on the following criteria: (1) abundance of aminoacyl-tRNAs for a particular codon in Lepidopteran species of insect cells for a given amino acid as described by Levin and Whittome (2000); (2) maintenance of GC-AT ratio in L1 gene sequence at approximately 1:1; (3) minimal introduction of palindromic or stem-loop DNA structures, and (4) minimal introduction of transcription and post-transcription repressor element sequences.

The optimized gene sequence was synthesized in vitro as overlapping oligonucleotides, cloned into a subcloning plasmid vector (pCR1), and then cloned into a bacmid transfer vector (pFASTBAC1) according to procedures known in the art (i.e., Luckow et al., 1993). The bacmid transfer vector with the L1 gene was used to transform competent *E. coli*/DH10BAC cells and produce recombinant bacmid DNA. The recombinant bacmid DNA with the L1 gene was transfected into insect cells to produce recombinant baculoviruses encoding L1 genes.

In particular, a restriction fragment (Bam HI/Sal I restriction fragment (1572 bp) containing a UPV-16 L1 gene (K strain)) containing a HPV L1 capsid gene from a natural virus isolate or synthesized gene is ligated to a bacmid transfer vector, such as pFASTBAC-1 (see, for example, Luckow et al., 1993), at the multiple cloning site, which contains a Tn7 transposable element surrounded by the transcription promoter and polyadenylation/transcription termination elements of the polyhedrin (polh) gene from a wild type AcMNPV genome, competent *E. coli* DH10BAC cells, which contain bacmid DNA (an AcMNPV baculovirus genome with a Tn7 transposable element within the polyhedrin locus), are transformed with the bacmid transfer vector containing the HPV L1 gene.

Recombinant bacmids are produced by site-directed recombination between the respective Tn7 transposable elements of the transfer vector and the bacmid genome resulting in the production of recombinant bacmid genomes encoding the optimized L1 gene in the *E. coli* hosts. The recombinant bacmid DNA is isolated for example by mini-prep DNA isolation and transfected into insect cells to produce recombinant baculoviruses encoding the L1 genes.

The progeny recombinant baculoviruses (~10$^4$ plaque forming units) are plaque-purified (3×) and selected for high expression of the BPV-16 L1 gene product, as determined by SDS-PAGE and Western blot analyses using rabbit polyclonal antisera specific for the HPV16 L1 gene product (Pharmingen). A HPV-16 L1 master virus stock is prepared in Sf-9S insect cells, as described in Example 2, from one of the plaque-purified clones expressing high levels of recombinant HPV-16 L1 proteins that self-assemble into virus-like particles and is qualified for safety and biological properties as described below. Working virus stocks of HPV-16 L1-expressing baculoviruses are prepared by infection of Sf-9S insect cells at a multiplicity of infection of 0.1 pfu/cell with the qualified HPV-16 L1 master virus stock and are characterized as described below to qualify for recombinant HPV-16 L1 VLP product manufacturing.

Example 4

Figure 1C:
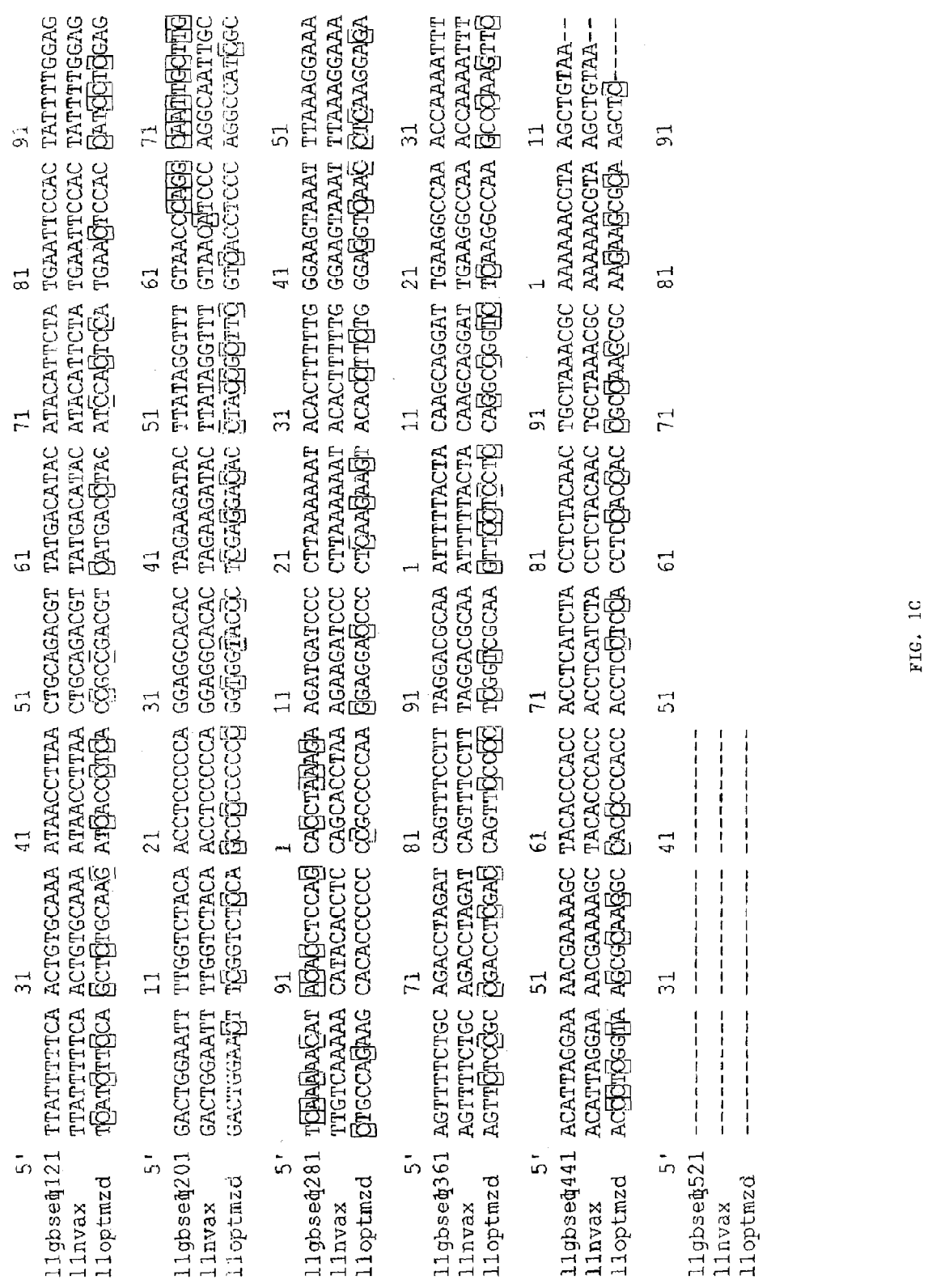

Cloning Codon-Optimized HPV-16 Chimeric Genes and Establishment of Chimeric Recombinant Baculovirus Stocks HPV-16 L2 fusion genes were optimized for codon usage in insect cells as described above for L1 genes (FIGS. 1C–1E). The L2/E7/E2 fusion gene sequences are synthesized in vitro as overlapping oligonucleotides, cloned into a subcloning plasmid vectors, and then cloned into a bacmid transfer vector according to procedures known in the art (i.e., Luckow et al., 1993).

For example, the bacmid transfer vector with the L2 fusion gene is used to transform competent E. coli DH10BAC cells and produce recombinant bacmid DNA. The codon-optimized gene is cloned into a bacmid transfer vector (i.e., Luckow et al., 1993).

In particular, a Bam HI/Kpn I restriction DNA fragment (2834 bp) containing a HPV-16 L2/E7/E2 fusion gene was ligated with T4 DNA ligase to a Bam HI/Kpn I digest of the bacmid transfer vector pFASTBAC-1 (Luckow et al., 1993) at the multiple cloning site. Competent E. coli DH10BAC cells were transformed with the bacmid transfer vector containing the HPV-16 L2/E7/E2 fusion gene.

Recombinant bacmids were produced by site-directed recombination between the respective Tn7 transposable elements of the transfer vector and the bacmid genome resulting in the production of recombinant bacmid genomes encoding the optimized HPV L1 gene in the E. coli hosts. The recombinant bacmid DNA was isolated by miniprep DNA isolation and transfected into Sf-9S insect cells to produce recombinant baculoviruses encoding the HPV-16 L1 gene.

The recombinant bacmid DNA was isolated by miniprep DNA isolation and transfected into Sf-9S insect cells to produce recombinant baculoviruses encoding the HPV-16 L2/E7/E2 L2 fusion genes. The recombinant baculoviruses were plaque-purified (3×) in Sf-9S insect cells and selected for high expression of the HPV-16 L2, E7, and E2 gene products, as determined by SDS-PAGE and Western blot analyses using antisera specific for each peptide within the L2 fusion gene product (HPV-16 L2, E7, and E2 peptides). A master virus stock of baculoviruses expressing HPV-16 L2/E7/E2 fusion proteins was prepared in Sf-9S insect cells from one of the plaque-purified clones expressing high levels of recombinant HPV L2 fusion proteins and was qualified for safety and biological properties. Working virus stocks of baculoviruses expressing HPV-16 L2/E7/E2 fusion proteins were prepared in Sf-9S insect cells at a multiplicity of infection of 0.1 pfu/cell with the qualified master virus stock and were tested.

Example 5

Characterization and Qualification of L1 and Chimeric Recombinant Baculovirus Stocks Recombinant baculovirus stocks for each of the HPV L1 and L2 fusion viruses were established. Master and working virus stocks were established from high expression virus clones and characterized for safety and biological properties. Safety properties of master and working virus stocks included microbial sterility, adventitious agent presence, endotoxin level, spiroplasma, and mycoplasma contaminants, and the like. Biological properties included genetic identity, virus titer, viral replication competence, and recombinant protein production competence. The genetic identity of the master virus stock was determined, for example, by DNA sequence analysis of both strands of bacmid DNA encoding the HPV L1 or L2 fusion genes and flanking sequences. The virus titer of master and working virus stocks were determined by an agarose plaque assay using insect cells and serial dilutions of the virus stock.

Viral replication competency was evaluated by passage of an aliquot of the virus stocks in insect cells at low multiplicity of infection. Subsequent determination of the virus titer for the progeny virus passage was performed by agarose plaque assay. Recombinant protein expression competency was evaluated, for example, by infection of insect cells with an aliquot of the virus stocks and subsequent determination of the relative abundance of recombinant proteins such HPV L1 and L2 fusion proteins per total cell protein in infected cells by SDS-PAGE analysis.

Example 6

Virus Infection for HPV-16 L1 VLPs

Recombinant HPV-16 L1 VLPs expressed in baculovirus-infected Sf-9S cells were purified from intracellular and extracellular crude lysates. Sf-9S insect cells from Example 2 were thawed from a single cryovial of the working cell bank frozen at −70° C. in Sf-900 II SFM insect cell media (GIBCO) at a concentration of $1.0 \times 10^7$ cells/ml. Thawed cells were seeded into 50 ml of Sf-900 II SFM insect cell media and cultured as suspension cultures in 500 ml shaker flasks in a platform shaker incubator at 28° C. with an agitation speed of 125 rpm.

After the cell density reached $6 \times 10^6$ cells/ml and a cell viability of more than 95%, the culture was seeded into two (2) liter flasks in a final volume of 800 ml of insect serum-free media per flask at a starting seed density of $0.5 \times 10^6$ cells/ml. The cells were cultured in a platform shaker incubator at 28° C. with an agitation speed of 100–125 rpm. When the cell density reached $2$–$3 \times 10^6$ cells/ml, the insect cells were infected with a recombinant baculovirus encoding the HPV-16 L1 capsid gene (K strain) from the polh locus made according to Example 3. The virus infection was established at a MOI of 3 pfu per cell. The virus infection was carried out for six days in a platform shaker incubator at 28° C. with an agitation speed of 125 rpm. The infected cells were harvested by centrifugation (at 1,500×g and 2–8° C. for 10 minutes) after the following conditions were met: cell viability was less than 25%, and L1 gene products were in culture fluids and within infected cells.

Example 7

Virus Infection for HPV-16 Chimeric VLPs

Production of intracellular HPV-16 L2/E7/E2 chimeric VLPs began with high multiplicity infection of log phase Sf-9S insect cells ($1.5 \times 10^6$ cells/ml) in suspension shaker flask cultures (2 L) containing serum-free insect cell medium (800 ml; HyQ SFM media, HyClone) made according to Example 2 with aliquots of HPV-16 L1 and L2/E7/E2 working virus stocks prepared according to Example 4. The ratio of co-infecting viruses was approximately 1:10 (L1 to L2 virus). The virus infection was monitored daily by the trypan blue exclusion method for cytopathic effects, cell viability, and cell density and by SDS-PAGE and Western blot analyses of recombinant HPV L1 and L2 fusion proteins in infected cells. At three days post-infection when peak recombinant HPV-16 L1 and L2/E7/E2 fusion gene expression occurred, infected cells containing intracellular HPV-16 chimeric VLPs were harvested by centrifugation at 1500×g and 2–8° C. for 5 minutes and processed to obtain purified HPV-16 chimeric VLP products.

All references discussed herein are incorporated by reference. One skilled in the art will readily appreciate that the present invention is well adapted to carry out the objects and obtain the ends and advantages mentioned, as well as those inherent therein. The present invention may be embodied in other specific forms without departing from the spirit or essential attributes thereof and, accordingly, reference should be made to the appended claims, rather than to the foregoing specification, as indicating the scope of the invention.

BIBLIOGRAPHY

Bosch, F. X., Manos, M. M., Munoz, N., Sherman, M., Jansen, A. M., Peto, J., Schiffman, M. H.,
Moreno, V., Kurman, R., Shah, K. V. (1995) Prevalence of human papillomavirus in cervical cancer: a worldwide prospective. J. Nat. Cancer Inst. 87:796–802
Breitburd, F., Kirnbauer, R., Hubbert, N. L., Normenmacher, B. Trin-Dinh-Desmarquet, C., Orth,
G., Schiller, J. T., and Lowy, D. R. (1993) Immunization with virus-like particles from cottontail rabbit papillomavirus (CRPV) can protect against experimental CRPV infection. J. Virol. 69:3959–3963
Christiansen, N. D., Hopfi, R., DiAngelo, S. L., Cladel, N. M., Patrick, S. D., Welsh, P. A.,
Budgeon, L. R., Reed, C. A., and Kreider, J. W. (1994) Assembled baculovirus-expressed human papillomavirus type 11 capsid protein virus-like particles are recognized by neutralizing monoclonal antibodies and induce high titters of neutralizing antibodies. J. Gen. Virol. 75:2271–2276.
Christensen, N. D., Reed, C. A., Cladel, N. M., Han, R., and Kreider, H. W. (1996) Immunization with virus-like particles induces long-term protection of rabbits against challenge with cottontail rabbit papillomaviruses. J. Virol. 70:960–965
Cook, J. C., Joyce, J. G., George, H. A., Schultz, L. D., Hurni, W. M., Jansen, K. U., Hepler, R. W.,
Ip, C., Lowe, R. S., Keller, P. M., and Lehman, E. D. 1999. Purification of Virus-like particles of recombinant human papillomavirus type 11 major capsid protein L1 from Saccharomyces cerevisiae. Protein Expression Purif 17: 477–484.
Greenstone, H. L., Nieland, J. D., de Visser, K. E. et al. (1998). Chimeric Papillomavirus-like Particles Elicit Antitumor Immunity Against the E7 Oncoprotein in an HPV 16 Tumor Model. Proc. Natl. Acad. Sci. USA 95, 1800–1805.
Hagensee, M. and Galloway, D. (1993) Growing human papillomaviruses and virus-like particles in the laboratory. Papillomavirus Report 4:121–124
Harro, C. D., Pang, Y.-Y. S., Roden, R. B. S., Hildesheim, A., Wang, Z., Reynolds, M. J., Mast,
T. C., Robinson, R., Murphy, B. R., Karron, R. A., Dillner, J., Schiller, J. T., and Lowy, D. R. (2001) Safety and immunogenicity trial in adult volunteers of a human papillomavirus 16 virus-like particle vaccine. J. Natl. Acad. Sci. 93:284–292.
IARC IAfRoC. Human Papillomaviruses. Vol. 64: WHO, 1995 (Cancer IAfRo, ed. IARC Monographs on the evaluation of carcinogenic risks to humans)
Joyce, J. G., Tung, J. S., Przysiecki, C. T., et al. (1999) The L1 major capsid protein of human papillomavirus type 11 recombinant virus-like particles interacts with heparin and glycosaminoglycans on human keratinocytes. J. Biol. Chem. 274:5810–5822.
Kirnbauer, R., Booy, F., Cheng, N., Lowy, D. R., and Schiller, J. T. (1992) Papillomavirus L1 major capsid protein self-assembles into virus-like particles that are highly immunogenic. Proc. Natl. Acad. Sci. USA 89: 12180–12184.
Kirnbauer, R., Taub, J., Greenstone, H., Roden, R., Durst, M., Gissman, L., Lowy, D. R., and
Schiller, J. T. Efficient self-assembly of human papillomavirus type 16 L1 and L1–L2 into virus-like particles. J. Virol. 67:6929–6936.
Kirnbauer, R., Chandrachud, L., O'Neil, B., Wagner, E., Grindlay, G., Armstrong, A., McGarvie, G., Schiller, J., Lowy, D., Campo, M., (1996) Viruslike particles of bovine papillomavirus type 4 in prophylactic and therapeutic immunization. Virology 219:37–44.
Kurman, R. J., Henson, D. E., Herbst, A. L., Noller, K. L., and Schiffman, M. H. (1994) Interim guidelines for management of abnormal cervical cytology. The 1992 National Cancer Institute Workshop. JAMA 271:1866–1869
Levin, D. B. and Whittome, B. (2000) Codon usage in nucleopolyhedroviruses. J. Gen. Virol. 81:2313–2325.
Luckow, V. A., Lee, S. C., Barry, G. F., and Olins, P. O. 1993. Efficient generation of infectious recombinant baculoviruses by site-specific transposon-mediated insertion of foreign genes into a baculovirus genome propagated in *Escherichia coli*. J. Virol. 67: 4566–4579.
O'Neil, P. F., and Balkovic, E. S. (1993) Virus harvesting and affinity-based chromatography. A method for virus concentration and purification. Bio/Technology 11: 173–178.
Parkin, D. M., Pisani P., and Ferlay, J. (1990) Estimates of worldwide incidence from 25 cancers. Intl. J. Cancer 80:827–841
Pisani, P., Parkin, D. M., Bray, F., and Ferlay, J. (1990) Estimates of the worldwide mortality from 25 cancers. Intl. J. Cancer 83:18–29
Richardson, C. D. (Ed.) (1995) Methods in Molecular Biology 39, "Baculovirus Expression Protocols" Humana Press, Inc. (New York)
Robinson, R. A., Burgess, W. H., Emerson, S. U., Leibowitz, R. S., Sosnovtseva, S. A., Tsarev, S., and Purcell, R. H. (1998). Structural characterization of recombinant hepatitis E virus ORF2 proteins in baculovirus-infected insect cells. Protein Expression and Purification 12: 75–84.
Rose, R. C., Bonnez, W., Reichman, R. C., and Garcea, R. L. (1993). Expression of human papillomavirus type 11 L1 protein in insect cells: in vivo and in vitro assembly of viruslike particles. J. Virol. 67:1936–44
Schiller, J. and Lowy, D. 1996. Papillomavirus-like particles and HPV vaccine development. Seminars in Cancer Biol. 7:373–382

Shah, K. V. and Howley, P. M. Papillomaviruses. (1996) In: Fields, B., Knipe, D. M., and Howley, P.M. Eds. Virology. Philadelphia: Lippincott-Raven, pp. 2077–2109

Summers, M. D. and Smith, G. E. 1987. A manual of methods for baculovirus vectors and insect cell culture procedures. Texas Agric. Exp. Station Bull. 1855: 1–57.

Suzich, J. A., Ghim, S., Palmer-Hill, F. J., White, W. I., Tamura, J. K., Bell, J., Newsome, J. A., Jenson, A. B., and Schlegel, R. (1995) Systemic immunization with papillomavirus L1 protein completely prevents the development of viral mucosal papillomas. Proc. Natl. Acad. Sci. USA 92:11553–11557

Walboomers, J. M., Jacobs, M. C., Manosm M. M., Bosch, F. X., Kummer, J. A., Shah, K. V., et al. (1999) Human papillomavirus is a necessary cause of invasive cervical cancer worldwide. J. Pathol. 189:12–19

Zhou, J., Stenzel, D. J., Sun, X.-Y., and Fraser, I. H. (1993) Synthesis and assembly of infectious bovine papillomavirus particles in vitro. J. Gen. Virol. 74: 763–768.

What is claimed is:

1. The cell line ATCC PTA-4047, or a clone or a transfectant thereof.

2. The cell line of claim 1 infected with a recombinant baculovirus, such that at least one recombinant gene product is extracellularly expressed.

3. The cell line of claim 2, wherein the at least one recombinant gene product is a viral gene product.

4. The cell line of claim 3, wherein the viral gene product is a viral capsid protein that self-assembles into virus-like particles.

5. The cell line of claim 4, wherein the virus-like particles comprise a viral gene product of an enveloped virus, a non-enveloped virus, or both.

6. The cell line of claim 5, wherein the virus-like particles are from a virus comprising rotavirus, calicivirus, papillomavirus, hepatitis C virus, hepatitis E virus, influenza virus, human immunodeficiency virus, or a combination thereof.

7. The cell line of claim 2, wherein the recombinant gene product is encoded by a human papillomavirus polynucleotide.

8. The cell line of claim 7, wherein the human papillomavirus polynucleotides are codon optimized for expression in the cell line.

9. The cell line of claim 8, wherein the human papillomavirus polynucleotides comprise SEQ ID NO. 1, SEQ ID NO. 2, SEQ ID NO. 3, SEQ ID NO.4, or SEQ ID NO. 5, or a polynucleotide that has at least 50% nucleotide sequence identity to any one of the SEQ ID NO. 1, SEQ ID NO. 2, SEQ ID NO. 3, SEQ ID NO. 4, or SEQ ID NO. 5, or a combination thereof.

* * * * *